(12) United States Patent
Riesbeck et al.

(10) Patent No.: US 6,423,316 B1
(45) Date of Patent: Jul. 23, 2002

(54) ANTICOAGULANT FUSION PROTEIN ANCHORED TO CELL MEMBRANE

(75) Inventors: Kristian Riesbeck, Malmö (SE); Anthony Dorling, London (GB); Andrew John Timothy George, Surrey (GB); Robert Ian Lechler, London (GB)

(73) Assignee: Imperial College Innovative Limited, London (GB)

( * ) Notice: Subject to any disclaimer, the term of this patent is extended or adjusted under 35 U.S.C. 154(b) by 0 days.

(21) Appl. No.: 09/402,515

(22) PCT Filed: Mar. 26, 1998

(86) PCT No.: PCT/GB98/00850
§ 371 (c)(1),
(2), (4) Date: Feb. 2, 2000

(87) PCT Pub. No.: WO98/42850
PCT Pub. Date: Oct. 1, 1998

(30) Foreign Application Priority Data

Mar. 26, 1997 (GB) .............................. 9706327
Sep. 23, 1997 (GB) .............................. 9720248

(51) Int. Cl.[7] .................. A61K 39/00; C12N 65/00; C07K 1/00; C07H 21/04

(52) U.S. Cl. .................. 424/192.1; 435/320.1; 530/350; 536/23.1; 536/23.4

(58) Field of Search .............................. 435/325, 320.1, 435/455; 530/350, 387.3; 514/44; 800/13; 536/23.1, 23.4; 424/192.1

(56) References Cited

FOREIGN PATENT DOCUMENTS

WO    WO 96/04378    *    2/1996

OTHER PUBLICATIONS

Palmiter et al., Science, vol. 222, p. 809–814, 1983.*
Prusel et al., J. Reprod. Fert. Suppl. 40: 235–245, 1990.*
Kappel et al., Current Opinion in Biotechnology, 3: 548–553, 1992.*
Louis–Marie Houdebine, Journal of Biotechnology, vol. 34, p. 269–287, 1994.*
Mastrangelo et al., Seminars in Oncology, vol. 23, No. 1, p. 4–21, Feb. 1996.*

* cited by examiner

Primary Examiner—Deborah J. R. Clark
Assistant Examiner—Shin-Lin Chen
(74) Attorney, Agent, or Firm—Darby & Darby

(57) ABSTRACT

The invention relates to the inhibition of blood coagulation, especially during organ rejection, and in particular the inhibition of delayed vascular rejection. The invention provides anticoagulant proteins which are anchored to cell membranes. The anticoagulant function preferably provided by heparin, antithrombin, hirudin, TFPI, tick anticoagulant peptide, or a snake venom factor. These anticoagulant proteins are preferably prevented from being constitutively expressed at the cell surface. In particular, expression at the cell surface is regulated according to cell activation, for instance by targeting the protein to a suitable secretory granule. Expression of these proteins renders cells, tissues and organs less vulnerable to rejection after transplantation (e.g. after xenotransplantation).

9 Claims, 36 Drawing Sheets (2 of 36 Drawing Sheet(s) Filed in Color)

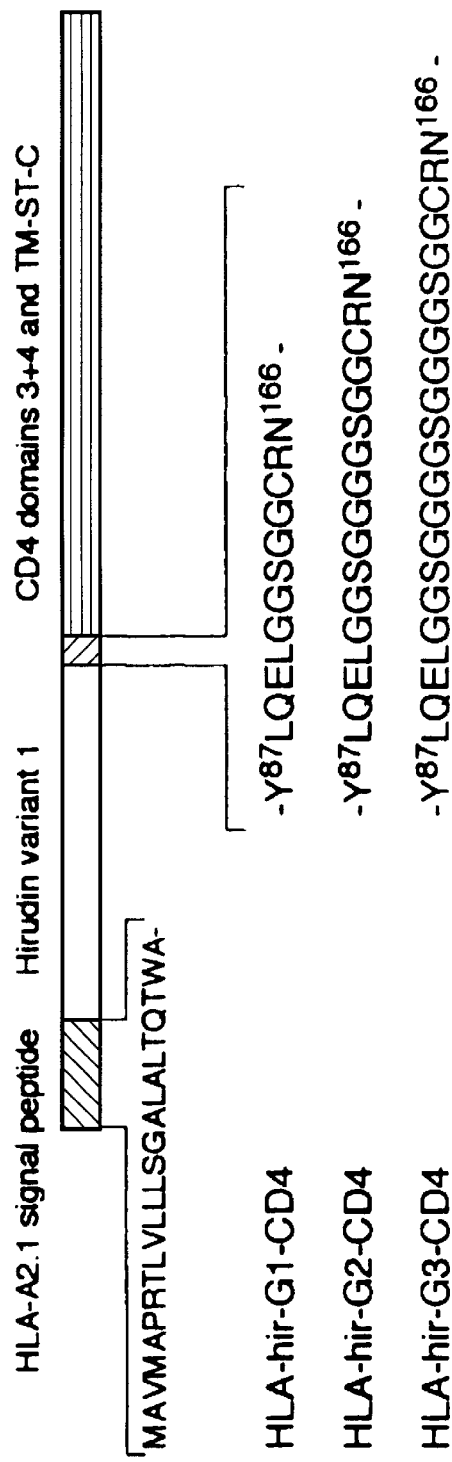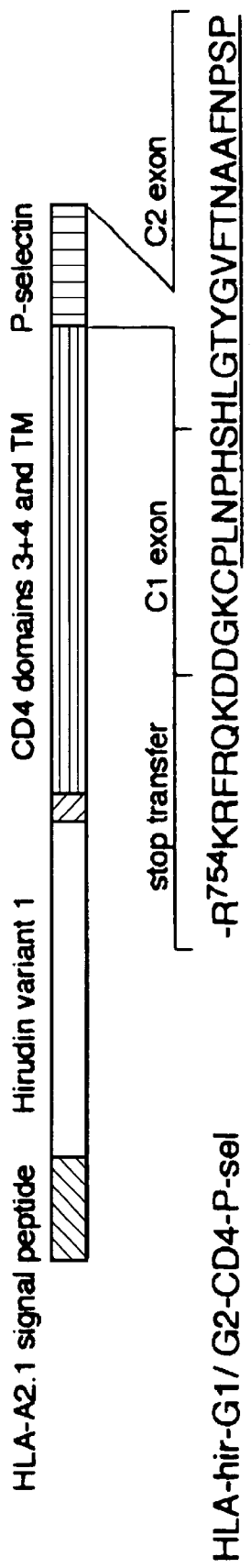
FIG. 1A
FIG. 1B

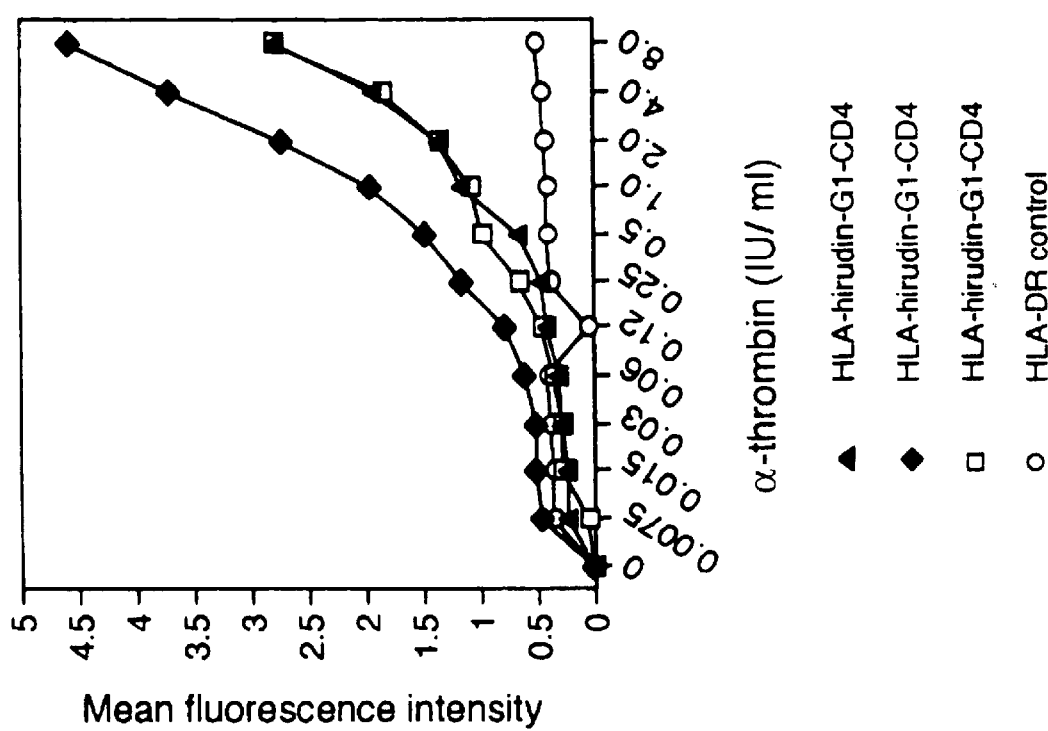
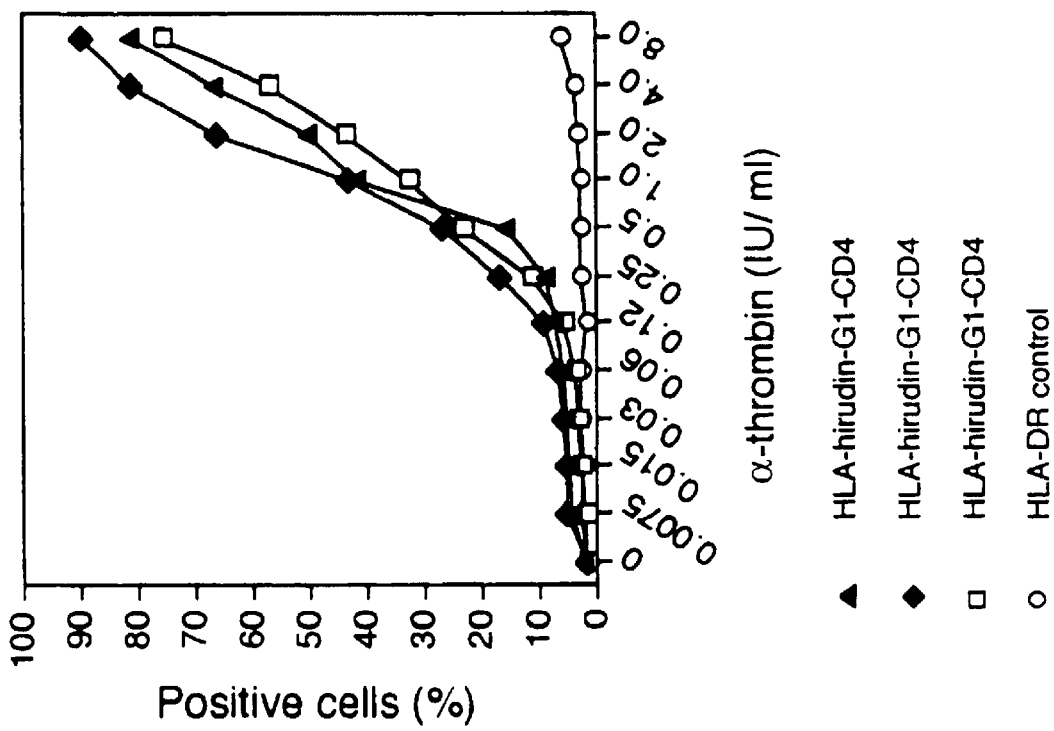

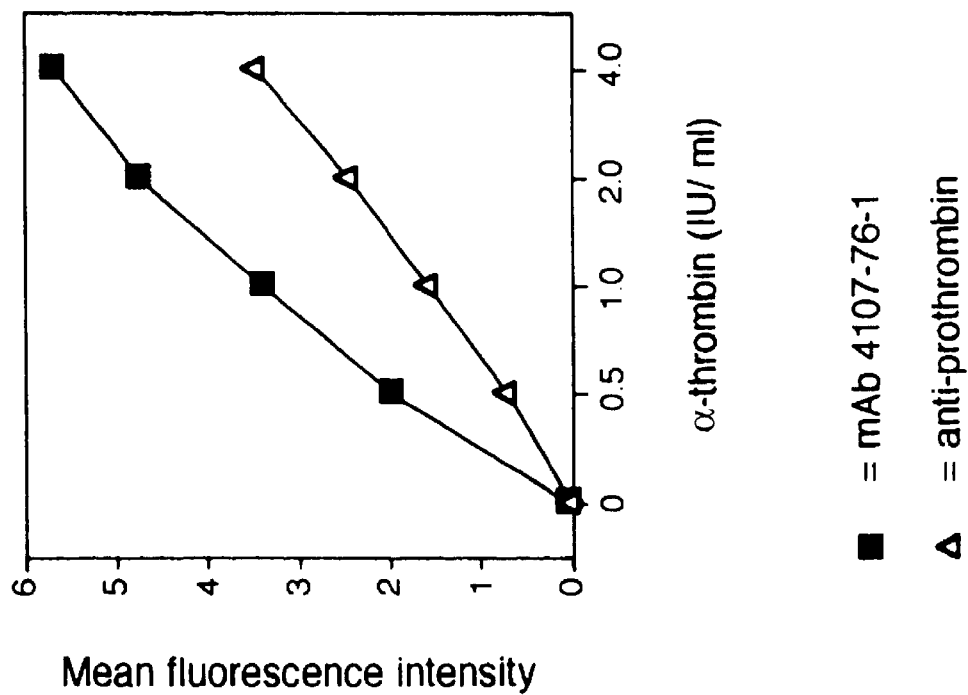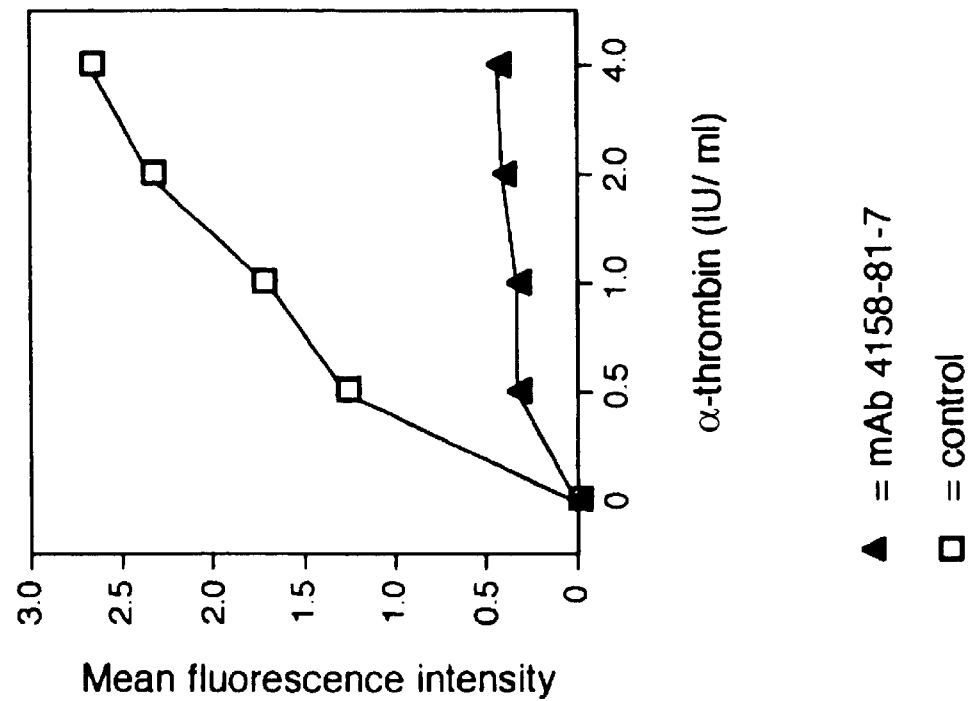

CHO-K1

DAP. 3

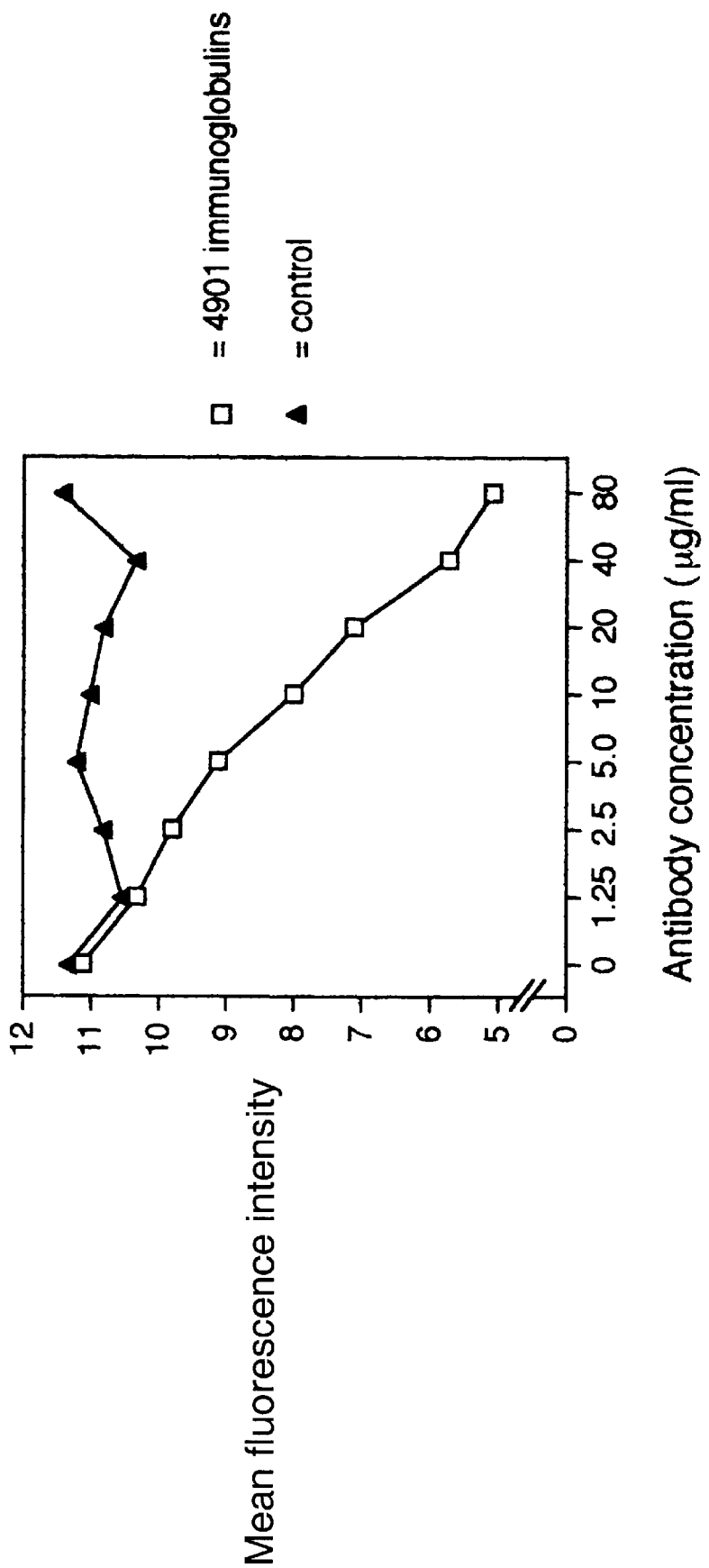

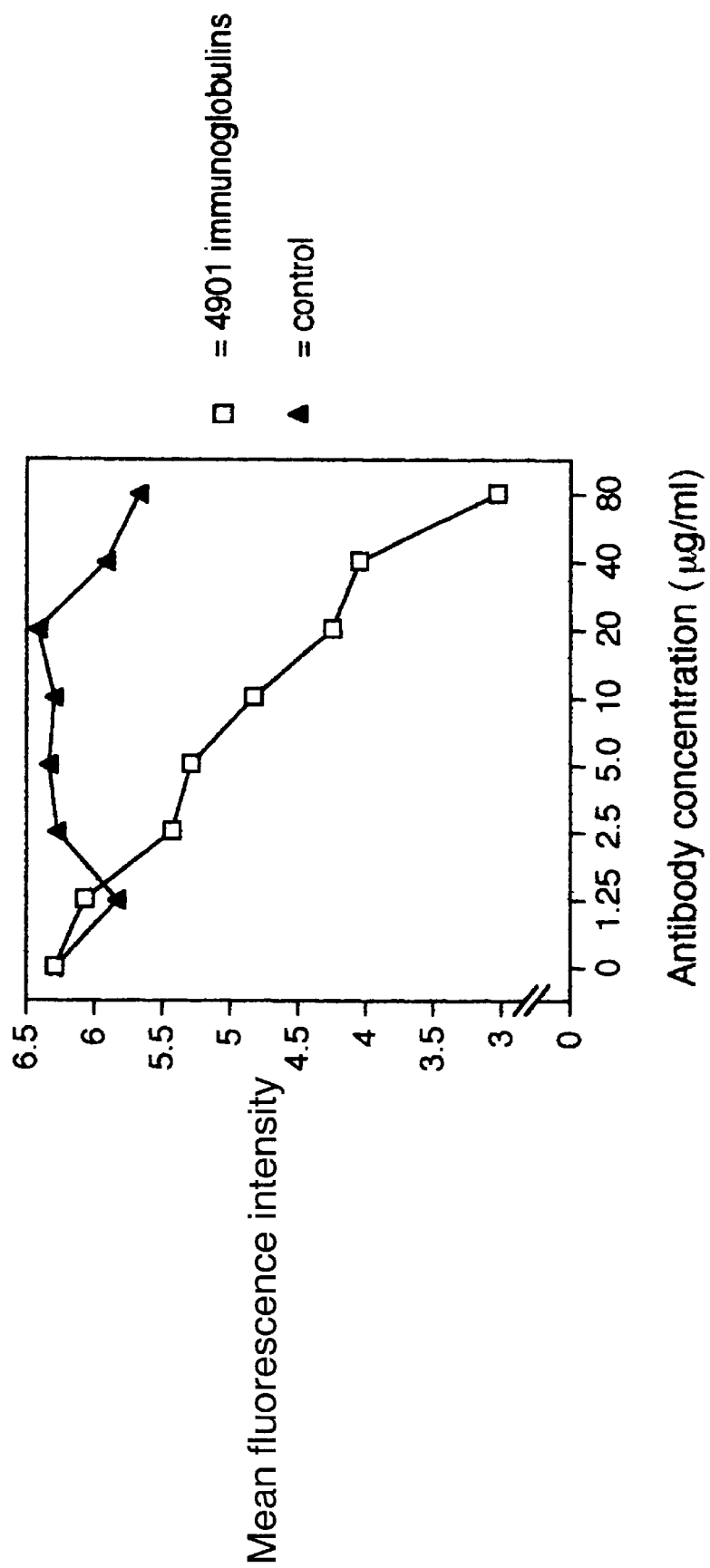

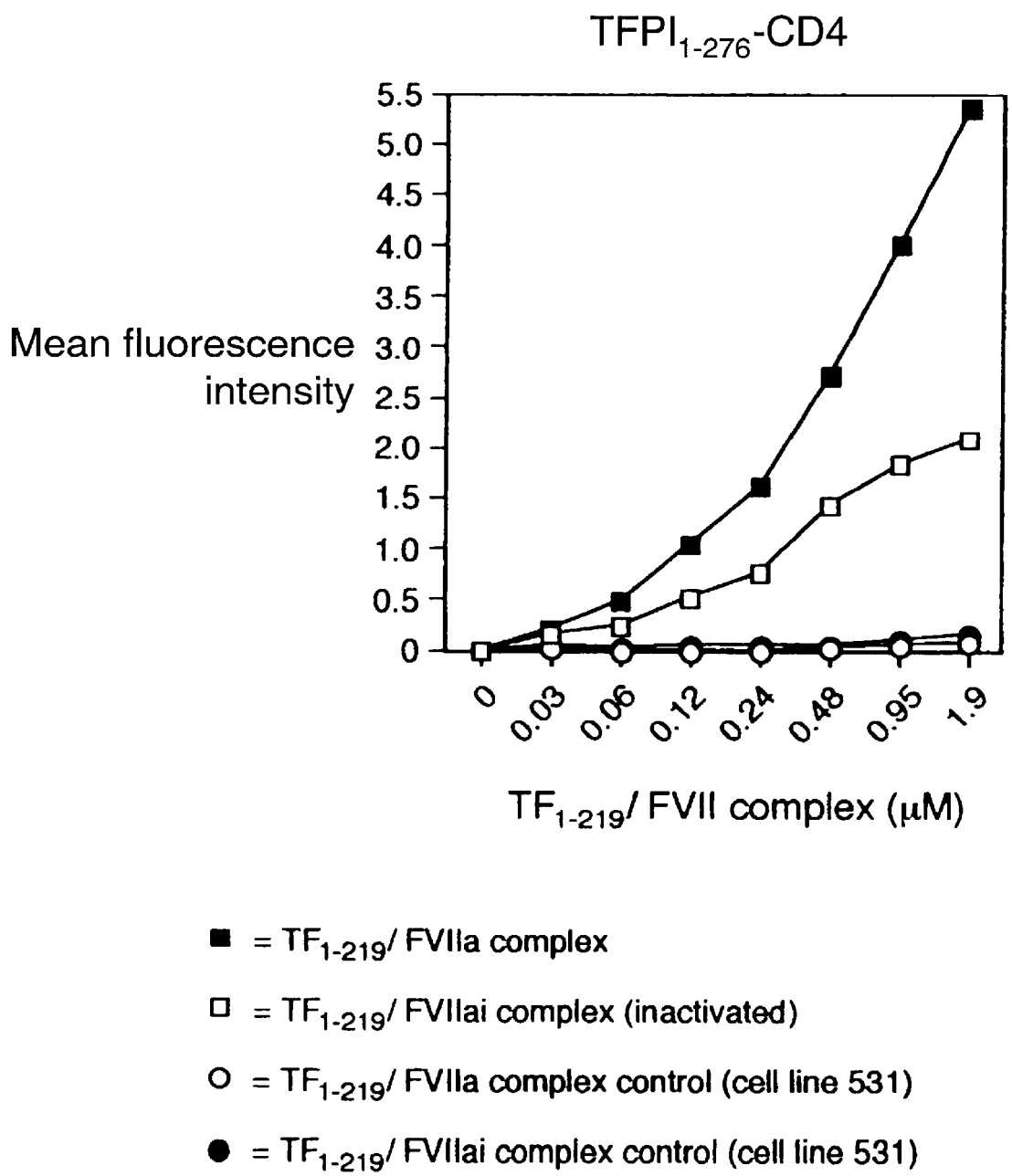

■ = TF$_{1-219}$/ FVIIa complex

□ = TF$_{1-219}$/ FVIIai complex (inactivated)

○ = TF$_{1-219}$/ FVIIa complex control (cell line 531)

● = TF$_{1-219}$/ FVIIai complex control (cell line 531)

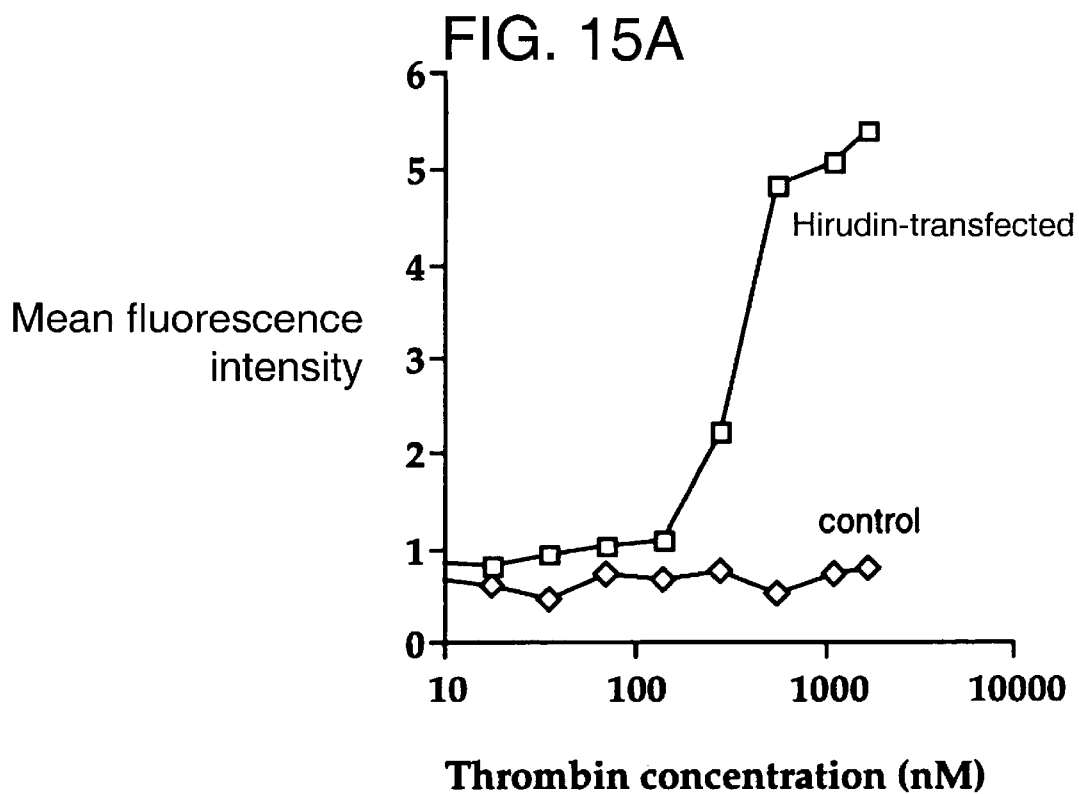
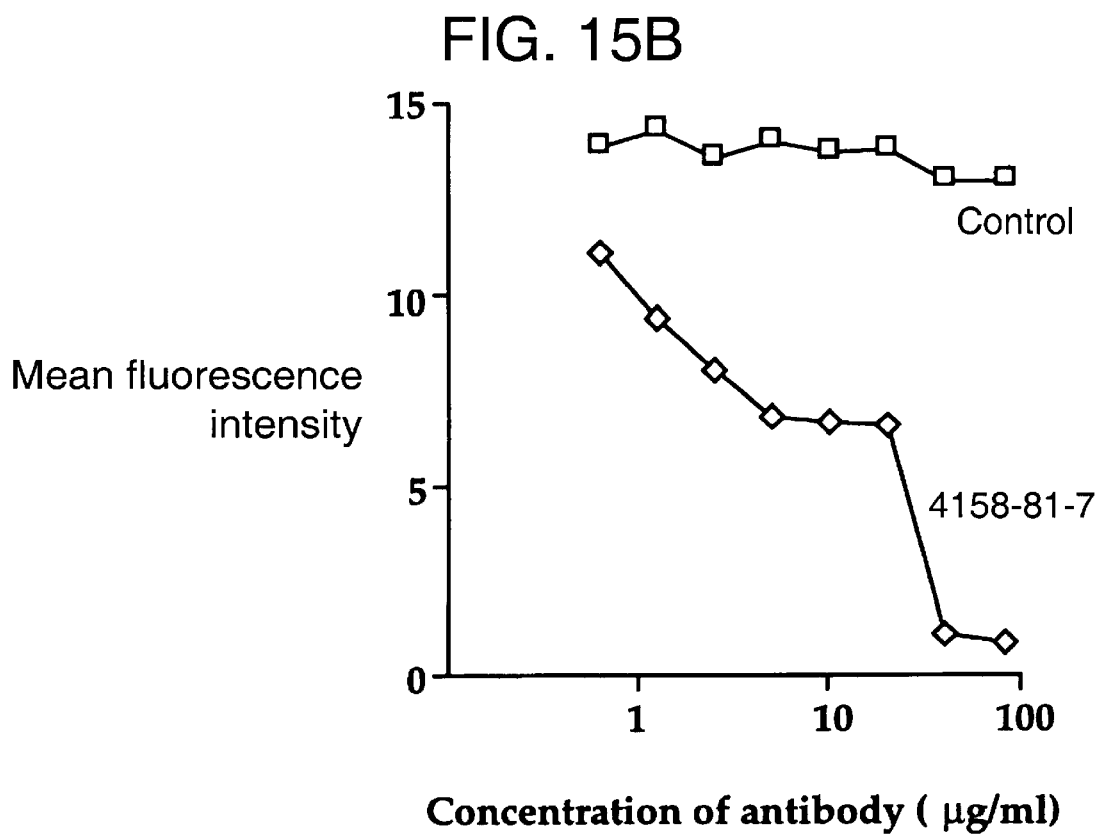

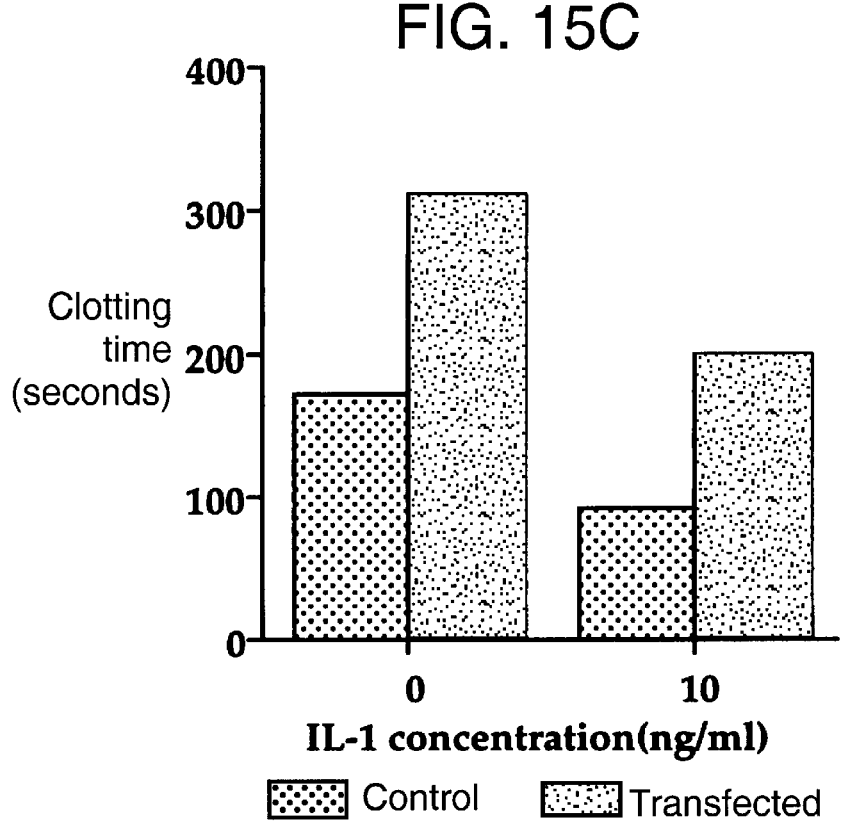
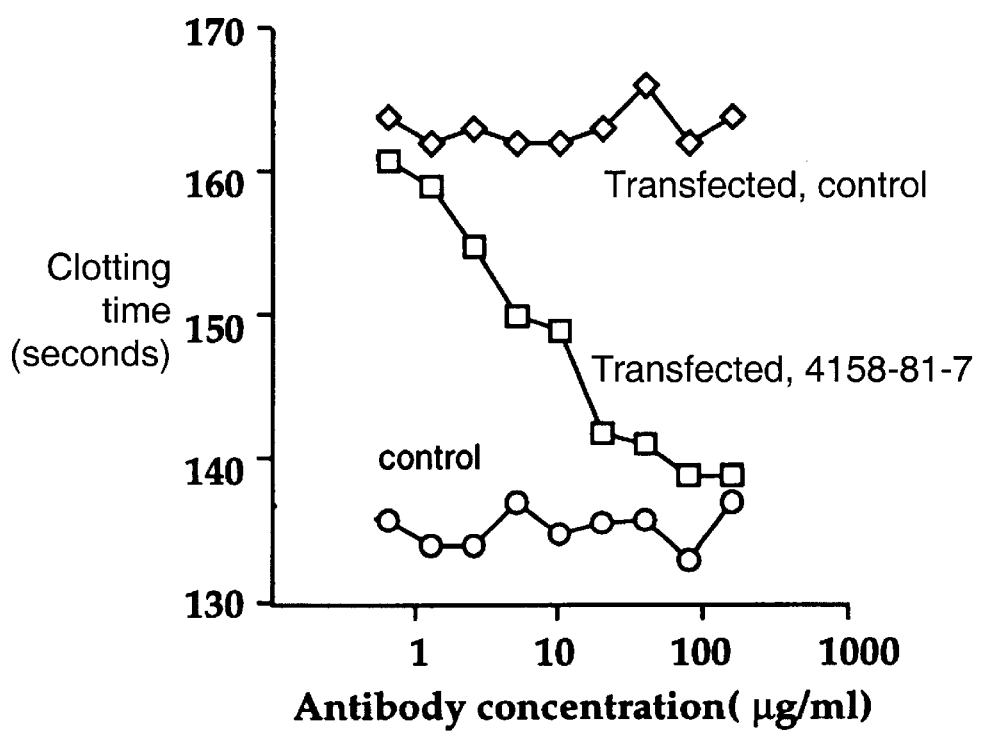

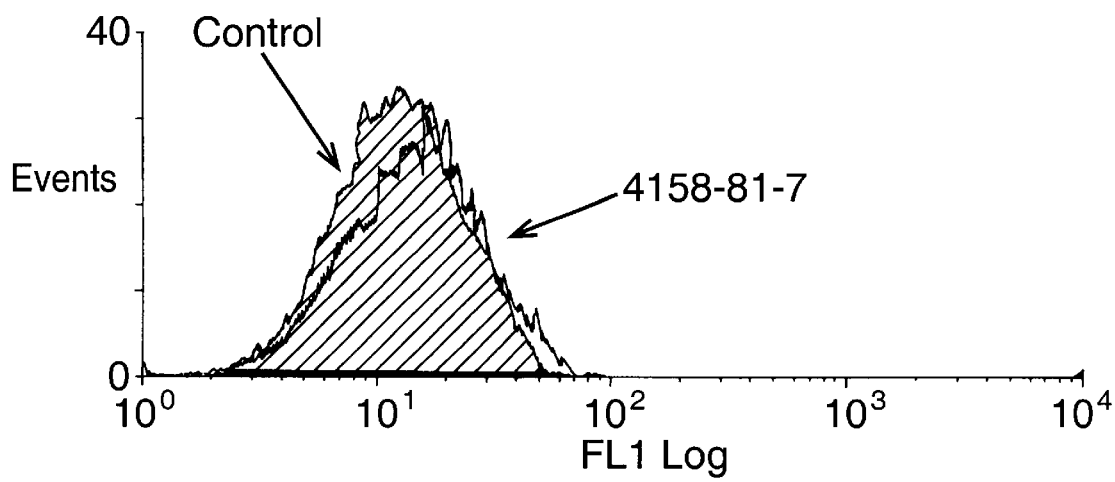
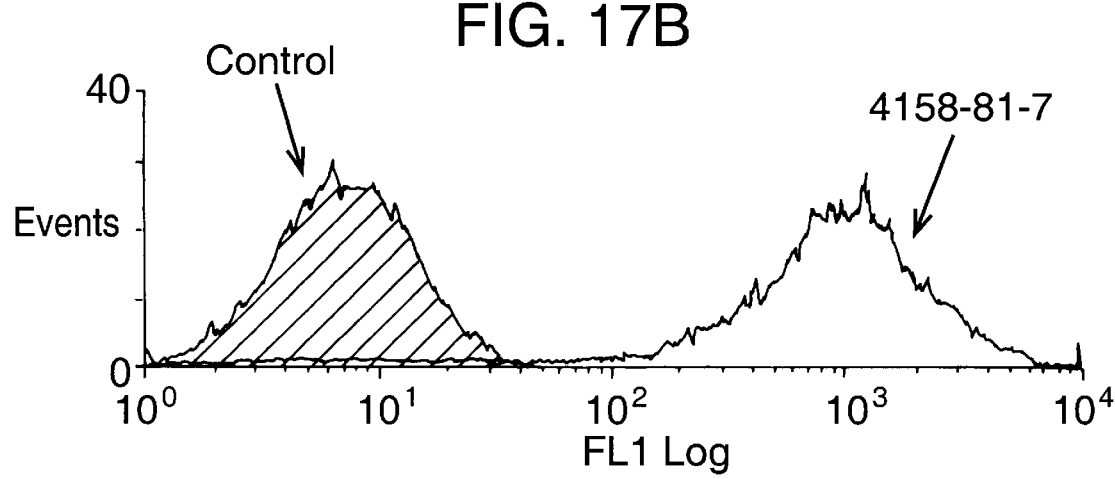
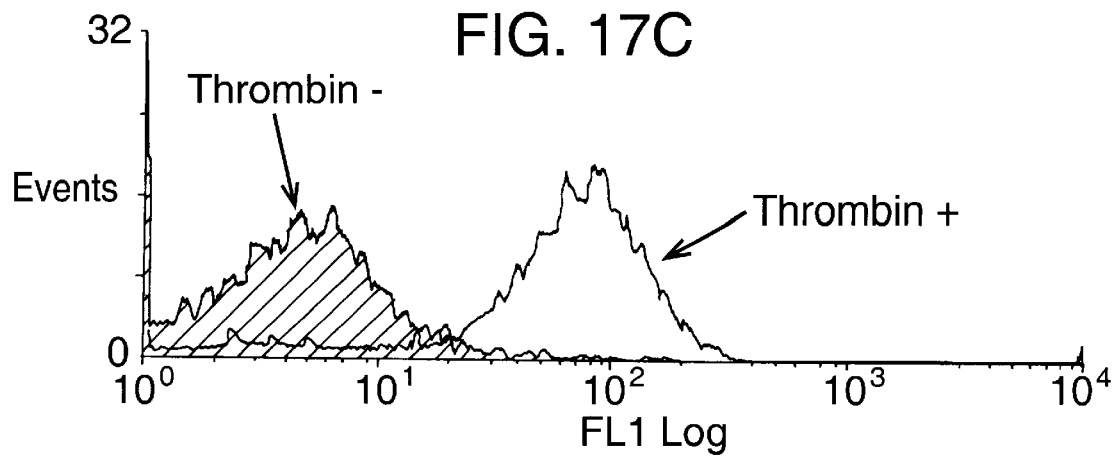

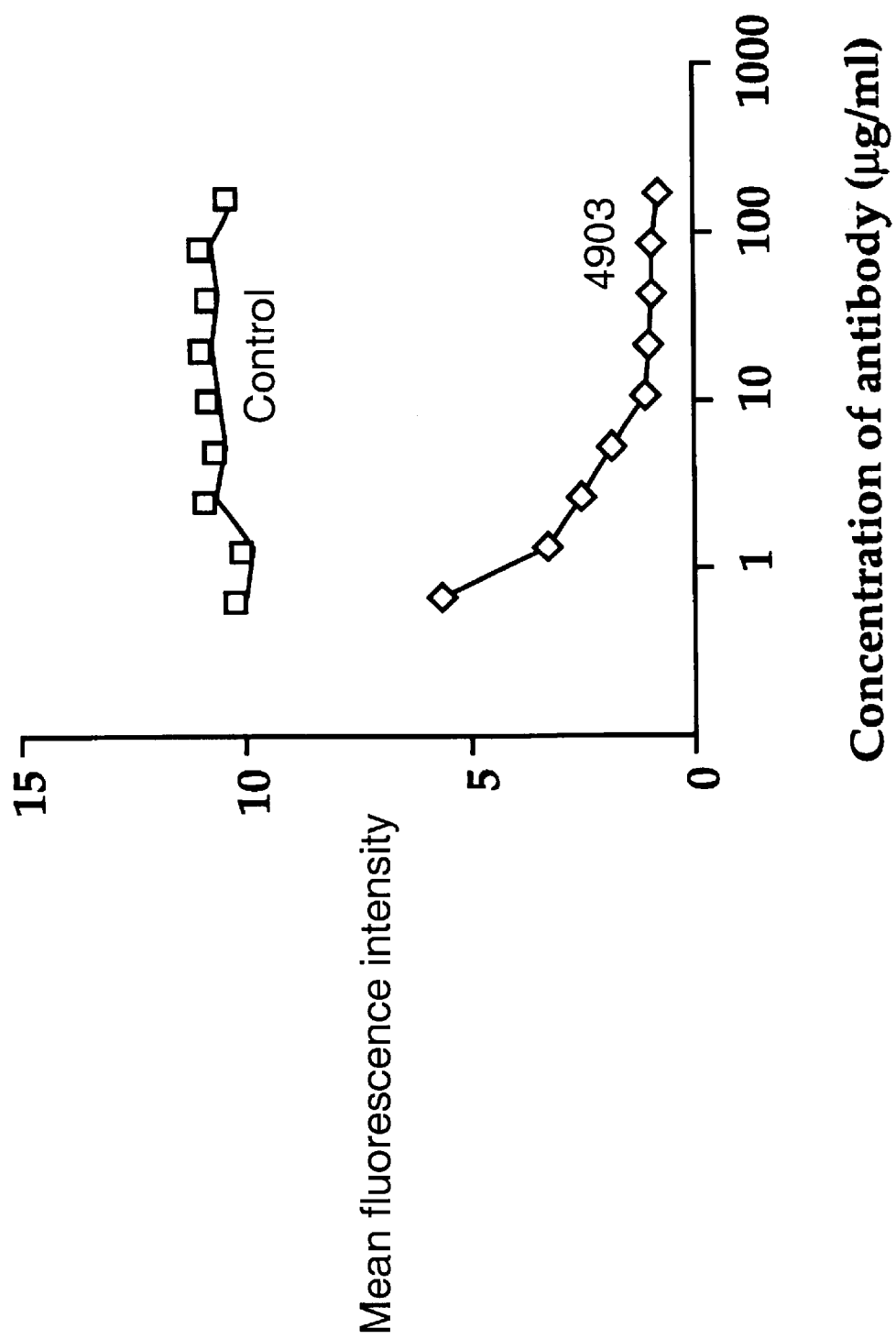

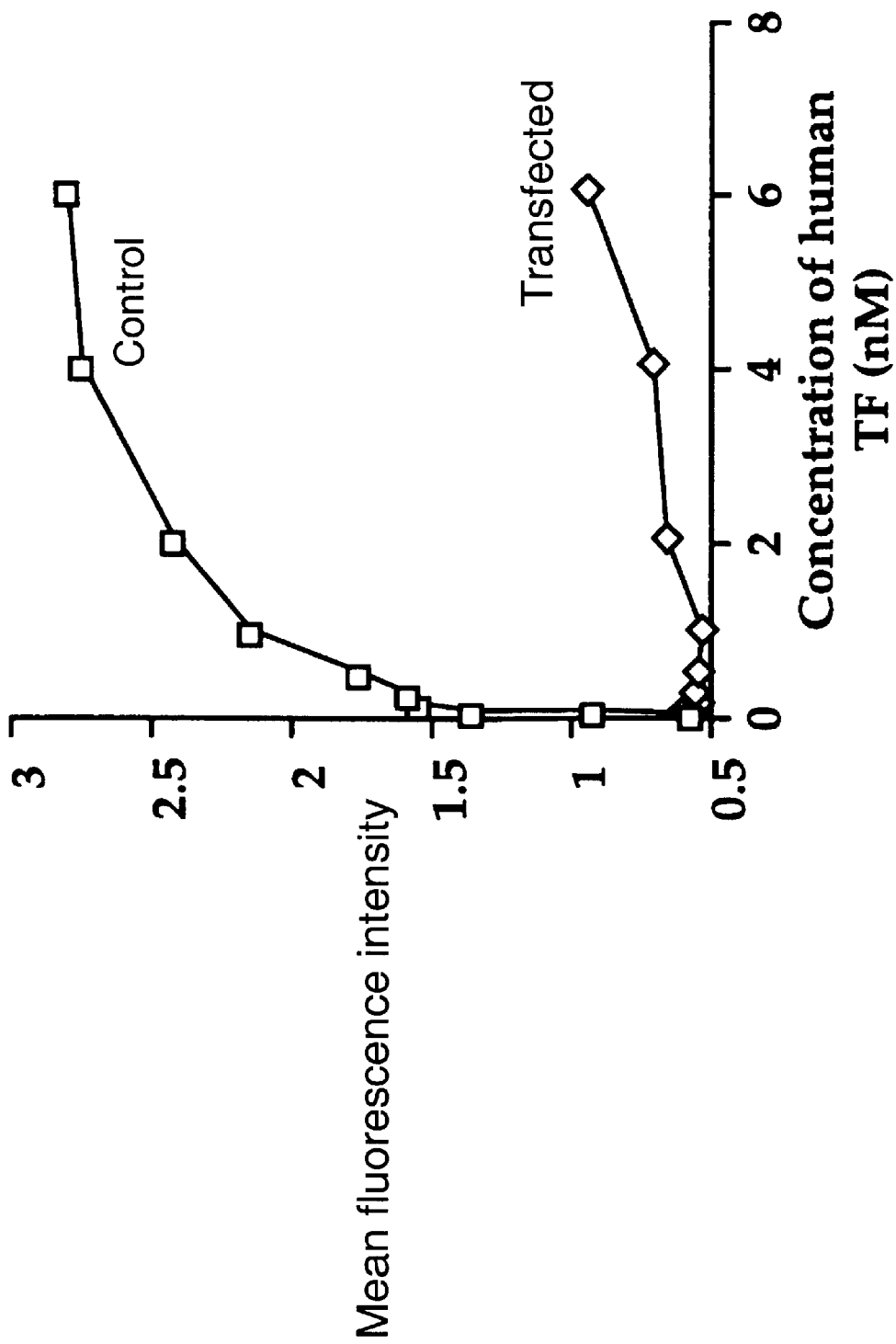

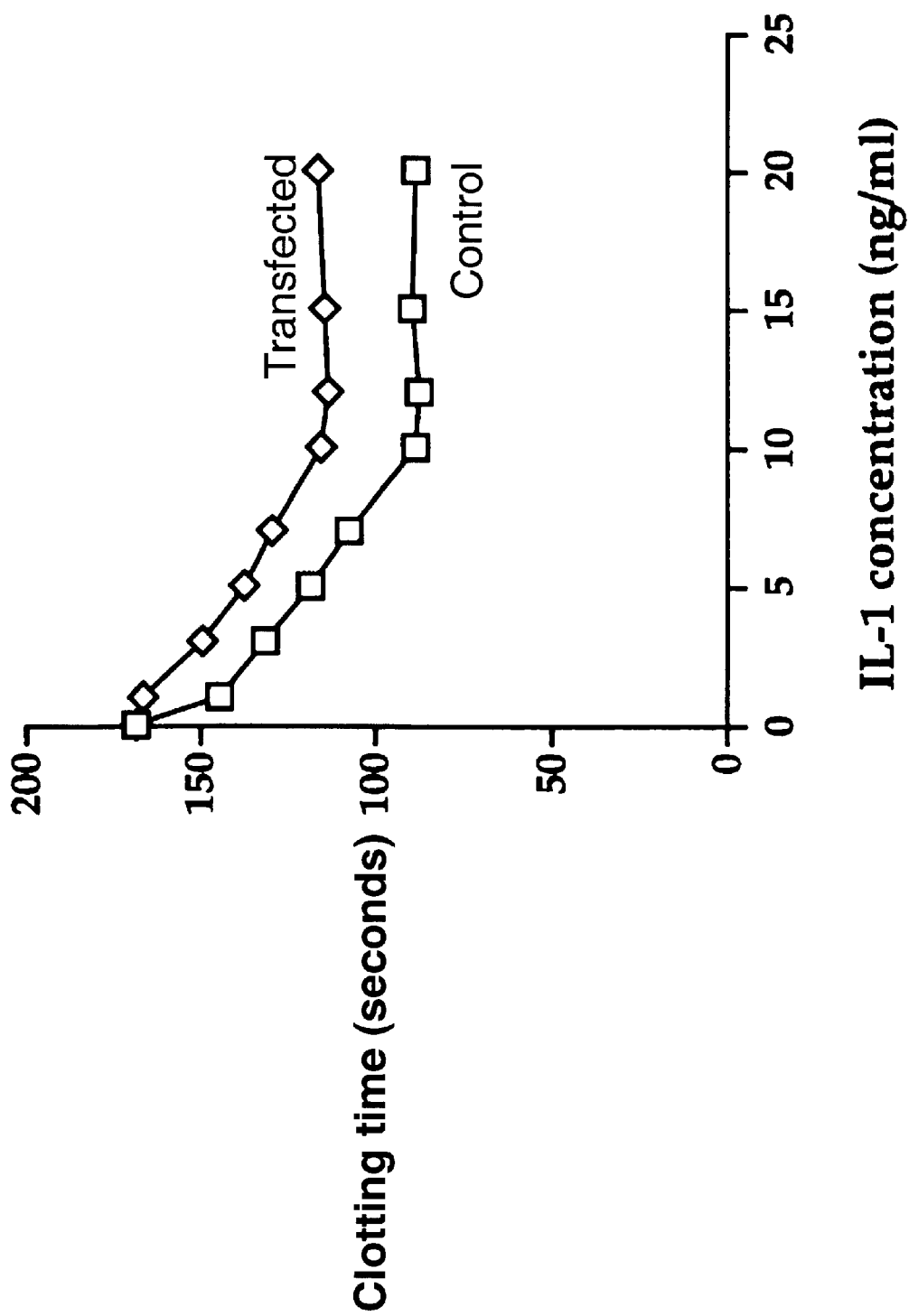

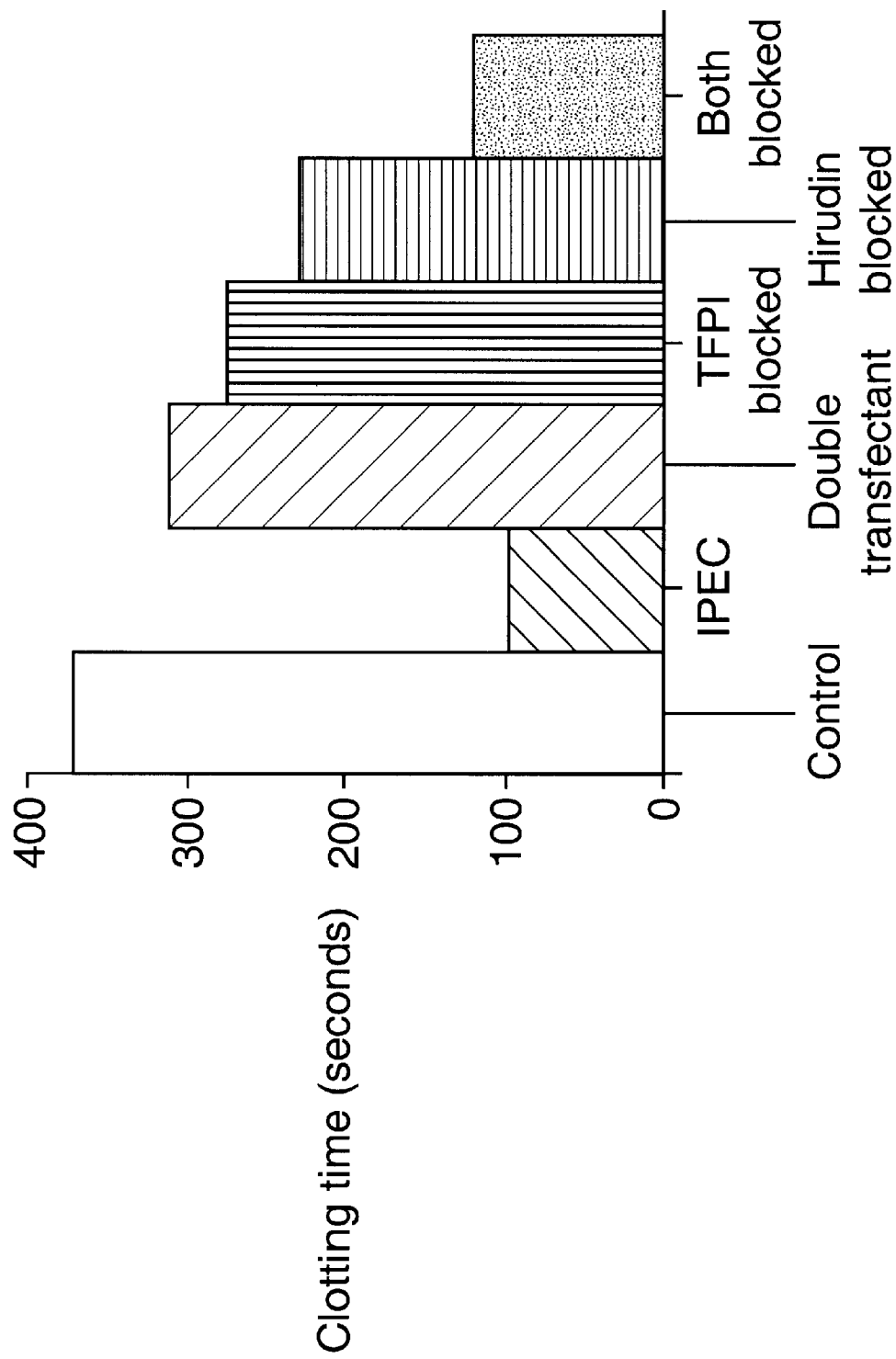

ANTICOAGULANT FUSION PROTEIN ANCHORED TO CELL MEMBRANE

FIELD OF THE INVENTION

This invention relates to the inhibition of blood coagulation, especially during organ rejection.

BACKGROUND TO THE INVENTION

The surgical technique of organ transplantation has now been successfully practised for several decades and, because of its success, the procedure has become widespread and, arguably, routine. However, the supply of suitable transplant organs is not able to match ever-rising demands.

Because of the shortage of suitable human (ie. allogeneic) organs, the possibility of using animal (ie. xenogeneic) organs in human transplant operations ("xenografting" or "xenotransplantation") has been receiving increased attention in recent years (eg. *Nature* 1997; 385:285). Porcine donor organs are thought to be suitable candidates because pigs are anatomically and physiologically similar to humans and are in abundant supply.

Xenografting is currently hindered, however, by the severe and well-documented problems of rejection. This process can be divided into distinct stages, the first of which occurs within minutes of transplantation. This is known as the hyperacute response and is caused by existing antibodies in the recipient which recognise and react with foreign antigens on the endothelial cells (ECs) of the xenograft. This recognition triggers the complement cascade which in turn leads to lysis and death of ECs of the transplant.

This initial hyperacute rejection is then reinforced by the delayed vascular response (also known as acute vascular rejection or delayed xenograft rejection). The lysis and death of ECs during the hyperacute response is accompanied by oedema and the exposure of adventitial cells, which constitutively express tissue factor (TF) on their surface. Tissue factor is thought to be pivotal in the initiation of the in vivo coagulation cascade, and its exposure to plasma triggers the clotting reactions. Thrombin and TNF-α become localised around the damaged tissue and this induces further synthesis and expression of TF by ECs.

The environment around resting ECs does not favour coagulation. Several natural coagulation inhibitors are associated with the extracellular proteoglycans of ECs, such as tissue factor pathway inhibitor, antithrombin III, and thrombomodulin. The recognition of the foreign tissue by xenoreactive natural antibodies (XNAs), however, causes the loss of these molecules.

Together with the exposure and induction of tissue factor, the anticoagulant environment around ECs thus becomes pro-coagulant.

The vascularised regions of the xenograft thus become sites of blood clots, a characteristic of damaged tissue. Blood flow is impaired and the transplanted organ becomes ischaemic. A fuller account of delayed vascular rejection can be found in Bach et al. (1996).

The use of xenogeneic organs in transplants is therefore hindered by an initial hyperacute rejection followed by a prolonged vascular rejection, possibly followed by T-cell mediated rejection. Inhibition of the mechanisms responsible for these rejections could facilitate the use of xenografts.

The simple administration of suitable inhibitors, however, is not a particularly suitable approach. Completely inhibiting complement in a recipient animal is tantamount to immunosuppression, leaving the subject prone to opportunistic infections. Similarly, inhibiting the coagulation cascade in a recipient will leave the animal susceptible to uncontrolled post-operative bleeding. Therefore the inhibitors should desirably be localised in the recipient to the site of the xenograft.

The prevention of hyperacute rejection is the subject of European patent 0495852 (Imutran). To make tissues more suitable for xenografting this patent teaches that they should be associated with homologous complement restriction factors, which prevent the complete activation of complement in the xenogeneic organ recipient.

This approach has been developed and applied in order to produce transgenic animals with organs designed to survive hyperacute rejection (Squinto, 1996). Transgenic mice expressing human CD59, a complement regulator, on cardiac ECs have been produced (Diamond, 1995). The human CD59 retained biological activity and complement was inhibited when transgenic hearts were perfused with human plasma.

Transgenic pigs expressing human DAF and/or CD59 have been reported (McCurry, 1996). Cardiac rejection took twice as long to occur with the transgenic xenografts than with controls.

Inhibiting delayed vascular rejection has not received the same attention, although inhibitors of the coagulation cascade are well known in the art and many have been well characterised.

For instance, tissue factor pathway inhibitor (TFPI) is known to inhibit the function of the active complex which is normally formed between tissue factor, factor VIIa, and factor Xa. TFPI is a 276 residue soluble polypeptide whose positively charged C-terminus binds to heparin sulphate in the proteoglycan layer of ECs. It has been notionally divided into three "Kunitz" domains: Kunitz domain I is responsible for binding tissue factor and factor VIIa; domain II binds factor Xa; but the functions of domain III are less clear (Hamamoto, 1993).

Tick anticoagulant peptide (TAP) is a specific and potent inhibitor of factor Xa. This 60 amino acid polypeptide has been purified from the soft tick *Ornithodoros moubata*.

Many snake venoms also contain anticoagulant polypeptides. For instance, a 231 amino acid protein C activator has been purified from the venom of the snake *Agkistrodon contortrix contortrix* (McMullen, 1989; Kisiel, 1987).

Hirudin is the anticoagulant protein utilised by the leech *Hirudo medicinalis* when extracting blood from its victim. It is highly potent and binds to thrombin at a 1:1 ratio with a dissociation constant in the femtomolar range. The active site of thrombin is masked in the stable complex and so the hirudin prevents fibrinogen breakdown, thus inhibiting clot formation.

One possible approach for localising anticoagulants to the site of rejection is to link hirudin to antibodies against E-selectin, which is expressed on the surface of ECs during cell activation. This approach has been shown to be effective in inhibiting clot formation in vitro (Kiely, 1995). Other possible strategies were recently reviewed by Bach et al. (1996).

P-selectin (also known as CD62) is also expressed on the surface of ECs during cell activation. During synthesis it is targeted to secretory storage granules in platelets and endothelial cells by sequences residing in its cytoplasmic domain (Disdier, 1992). In response to cell agonists, such as thrombin, the granules are rapidly redistributed and P-selectin is expressed on the cell surface (Green, 1994).

It is an object of the present invention to provide membrane-bound anticoagulant proteins. These proteins are suitable for inhibiting the clotting cascade at the surface of ECs, thus inhibiting in vivo mechanisms responsible for organ rejection.

It is a further object to provide regulated expression of such molecules on the surface of ECs such that coagulation inhibition occurs locally during conditions of organ rejection. The rejection might be xenogeneic or allogeneic.

It is yet a further object of the invention to provide biological tissue suitable for transplantation, particularly for xenotransplantation.

DESCRIPTION OF THE INVENTION

According to a first aspect of the present invention there is provided a protein comprising a region with anticoagulant activity and a region which can anchor said protein to a cell membrane. Preferably this is a chimeric protein, that is to say the anchor region and anticoagulant region are derived from different proteins.

The anticoagulant region can comprise the sequence of any anticoagulant polypeptide. Examples of such anticoagulant polypeptides include heparin, TAPs, antithrombin, hirudins, and TFPIs, along with their functional derivatives, such as fragments and derivatives which retain anticoagulant activity. Anticoagulant derivatives of thrombin, normally a procoagulant, have also been reported (Dang, 1997).

Preferably the anticoagulant region comprises the sequence of a hirudin. Hirudins include hirudin, hirudin derivatives, analogs ("hirulogs"), and variants (eg. hirudisins). For instance, it has been reported that sulphation at Tyr-64 increases the anticoagulant activity of hirudin, and that hirudisin-2 is a more potent inhibitor of thrombin activity than hirudin itself (eg. Knapp, 1992; Skern, 1990).

As an alternative, the anticoagulant region might comprise the sequence of a tissue factor pathway inhibitor (TFPI). TFPIs include TFPI itself and derivatives or analogs thereof which retain inhibitory activity. Preferably the TFPI sequence comprises Kunitz domains I and II of TFPI itself.

As a further alternative, the anticoagulant region might comprise the sequence of a tick anticoagulant peptide (TAP). TAPs include TAP itself and derivatives or analogs thereof which retain inhibitory activity. For instance, the potency of FXa inhibition by TAP has been enhanced by site-directed mutagenesis (eg. Mao, 1995).

Further alternative anticoagulant regions could, for instance, comprise the sequence of a protein C activator, such as those isolated from snake venom (eg. McMullen, 1989; Kisiel, 1987), or the sequence of anticoagulants isolated from snake venoms which act other than via protein C activation, or their derivatives or analogs which retain anticoagulant activity.

The anchor region can be any entity which can attach the protein to a cell membrane. Suitable examples include transmembrane sequences from membrane proteins and GPI anchors. Preferably the anchor region is a sequence capable of attaching the protein to a lipid bilayer, such as the transmembrane regions of the HLA class I or CD4 proteins. It may also be desirable for the protein to comprise the cytoplasmic domain which is usually associated with said transmembrane regions, such as the CD4 cytoplasmic domain, and/or the extracellular domains immediately juxtaposed with the cell membrane, such as CD4 domains 3 and 4. Alternatively the anchor region might be a sequence conferring on the protein the ability to associate extracellularly with a membrane protein without the protein itself being inserted into the cell membrane.

According to a second aspect of the invention, there is provided a protein according to the first aspect further comprising a targeting sequence which prevents the protein from being constitutively expressed at the cell surface.

Preferably the targeting sequence is a polypeptide sequence which can target a nascent polypeptide to a secretory granule, and more preferably the secretory granule is one which does not fuse with the cell's plasma membrane until the cell is suitably stimulated. For example, Weibel-Palade bodies do not fuse with the plasma membrane until the endothelial cell surface is stimulated by a secretagogue, such as thrombin or fibrin (Wagner, 1993). Preferably the secretory granule fuses with the plasma membrane during EC activation which occurs during organ rejection.

Thus the targeting sequence is preferably one which targets a nascent polypeptide to a Weibel-Palade body, such as the relevant sequence from P-selectin. Most preferably the protein according to the second aspect of the invention comprises an anticoagulant sequence and the transmembrane and cytoplasmic domains of P-selectin. The domains from P-selectin thus provide both the anchor sequence and the targeting sequence.

According to a third aspect of the invention, there is provided a polynucleotide encoding a protein according to the present invention. Preferably the polynucleotide is DNA.

Preferably the polynucleotide comprises sequences suitable for the regulation of expression of protein according to the invention. This expression can preferably be controlled, such as cell-specific control, inducible control, or temporal control. For instance, expression might be specific for ECs, or might be regulated in response to cell activation.

According to a fourth aspect of the invention, there is provided a vector comprising a polynucleotide according to the third aspect.

The term "vector" signifies a molecule which is capable of transferring a polynucleotide to a host cell. Preferably the vector is a DNA vector and, more preferably, is capable of ex pressing RNA encoding a protein according to the invention. Numerous suitable vectors are known in the art.

Preferably the vector is suitable for the production of a transgenic animal. Vectors suitable for the generation of transgenic pigs, for example, are described in Heckl-Östreicher (1995), McCurry (1996), White (1995), Yannoutsos (1995), and Langford (1996). Minigene vectors suitable for the generation of transgenic mice are described in Diamond (1995).

According to a fifth aspect of the invention, there is provided a delivery system comprising a molecule of the first, second, third, or fourth aspects and means to deliver said molecule to a target cell.

Certain vectors according to the fourth aspect may also function as suitable delivery systems. Likewise, certain delivery systems according to this fifth aspect may also inherently be vectors, but this is not always the case. For instance, a viral vector can also function as a delivery system, whereas a liposomal delivery system is not a vector.

The delivery system may be viral or non-viral. Non-viral systems, such as liposomes, avoid some of the difficulties associated with virus-based systems, such as the expense of scaled production, poor persistence of expression, and concerns about safety. Preferably the delivery system is suitable for use in gene therapy. Numerous appropriate delivery systems are known in the art.

Preferably, the delivery system will be targeted so that molecules according to the present invention are taken up by cells suitable for transplantation, or cells which have been transplanted. More preferably the delivery system will be specific for these cells. For example, the delivery system may be targeted to a specific organ, such as the heart or the kidney, or to a specific cell type, such as endothelial cells.

To achieve this the delivery system may, for example, be a receptor-mediated delivery system, being targeted to receptors found on target cells. For example, the delivery system may be targeted to receptors found on heart cells, preferably to receptors found exclusively on heart cells, or it may be targeted to receptors found on endothelial cells, preferably to receptors found exclusively on endothelial cells, or to receptors found on activated endothelial cells, such as E-selectin or P-selectin.

The delivery system is preferably suitable for the generation of transgenic animals. For example, the delivery system may be targeted to a gamete, a zygote, or an embryonic stem cell.

According to a sixth aspect of the invention, there is provided a method of transfecting a cell with a vector according to the invention. This may involve the use of a delivery system according to the invention.

The cell type is not restricted and may be prokaryotic or eukaryotic. Transfection can occur in vivo or ex vivo.

Where the cell is for use in transplantation, the cell is preferably eukaryotic, more preferably an endothelial cell. The stable transfection of porcine endothelial cells, for example, is described in Heckl-Östreicher (1995).

Preferably, the cell is suitable for the generation of a transgenic animal. More preferably, the cell is a gamete, a zygote, or an embryonic stem cell. The transfection of murine ova by microinjection to generate transgenic mice, for example, is described in Diamond (1995), and the microinjection of porcine zygotes, for instance, to generate transgenic pigs is described in Yannoutsos (1995), Langford (1996), and White (1995).

According to a seventh aspect of the invention, there is provided a cell transfected according to the sixth aspect.

To increase the efficacy of inhibition of the coagulation cascade, the cell is preferably able to express two or more different proteins according to the invention, each of which inhibits the coagulation cascade at a different stage. For example, the anticoagulant region in one protein might comprise a TFPI, whilst in the other it comprises a hirudin.

According to an eighth aspect of the invention, there is provided biological tissue comprising a cell according to the invention. The term "biological tissue" as used herein includes collections of cells, tissues, and organs. Accordingly the definition includes, for example, fibroblasts, a cornea, nervous tissue, a heart, a liver, or a kidney.

According to a ninth aspect of the invention, there is provided an animal comprising a cell and/or biological tissue according to the invention. Preferably the animal is suitable for the production of organs for transplantation into humans. Preferably the animal is a mammal, and more preferably it is a transgenic pig or a transgenic sheep.

The animal might be treated whilst alive such that it comprises transgenic biological tissue (i.e. treated by gene therapy). Preferably, a live animal is transfected with a vector according to the invention in order to produce a transgenic animal. For example, a vector according to the invention could be specifically delivered to endothelial cells in a pig to produce transgenic organs suitable for xenotransplantation.

Alternatively, the animal might be born as a transgenic animal. Various suitable approaches for generating such transgenic animals are known in the art (eg. Bradley & Liu, 1996; Clarke, 1996; Wheeler, 1994). For example, direct manipulation of the zygote or early embryo, by microinjection of DNA for instance, is well known, as is the in vitro manipulation of pluripotent cells such as embryonic stem cells. Retroviral infection of early embryos has proved successful in a range of species, and adenoviral infection of zona-free eggs has been reported. Transgenesis and cloning of sheep by nuclear transfer has also been described (eg WO97/07668).

According to a tenth aspect of the invention, there is provided a method of rendering biological tissue suitable for transplantation, comprising expressing one or more proteins according to the present invention in said biological tissue, preferably in its endothelial cells. The biological tissue may be so rendered either in vivo or ex vivo. For example, an animal organ may be in vivo transfected with a vector according to the invention, or an organ could be transfected ex vivo before transplantation or in vivo after transplantation.

According to an eleventh aspect of the invention, there is provided a method of transplantation comprising transplanting biological tissue according to the invention from a donor animal into a recipient animal. Preferably the method is for xenotransplantation and the donor biological tissue is xenogeneic with respect to the recipient animal.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 5 shows the specificity of thrombin binding to cells expressing hirudin-CD4.

FIG. 11 shows the blocking of FXa binding by a polyclonal anti-TFPI immunoglobulin fraction.

FIGS. 15A–D shows the specificity of thrombin binding to immortalised porcine endothelial cells (IPEC) expressing hirudin-CD4, and also shows the effect of cell-surface hirudin-CD4 expression on clotting times.

FIGS. 17A–C shows the change in cellular distribution of hirudin-CD4-P-selectin after PMA stimulation FIGS. 18A–B shows that TFPI-CD4 expressed on IPEC retains its binding properties.

FIGS. 19A–B shows the competitive binding of porcine and human tissue factors.

FIGS. 20A–B shows that TFPI-CD4 prolongs clotting times when expressed on IPEC surface.

FIGS. 21A–B shows the anti-coagulant effect of co-expression of TFPI-CD4 and hirudin-CD4.

DESCRIPTION OF EMBODIMENTS

Figure 1C:
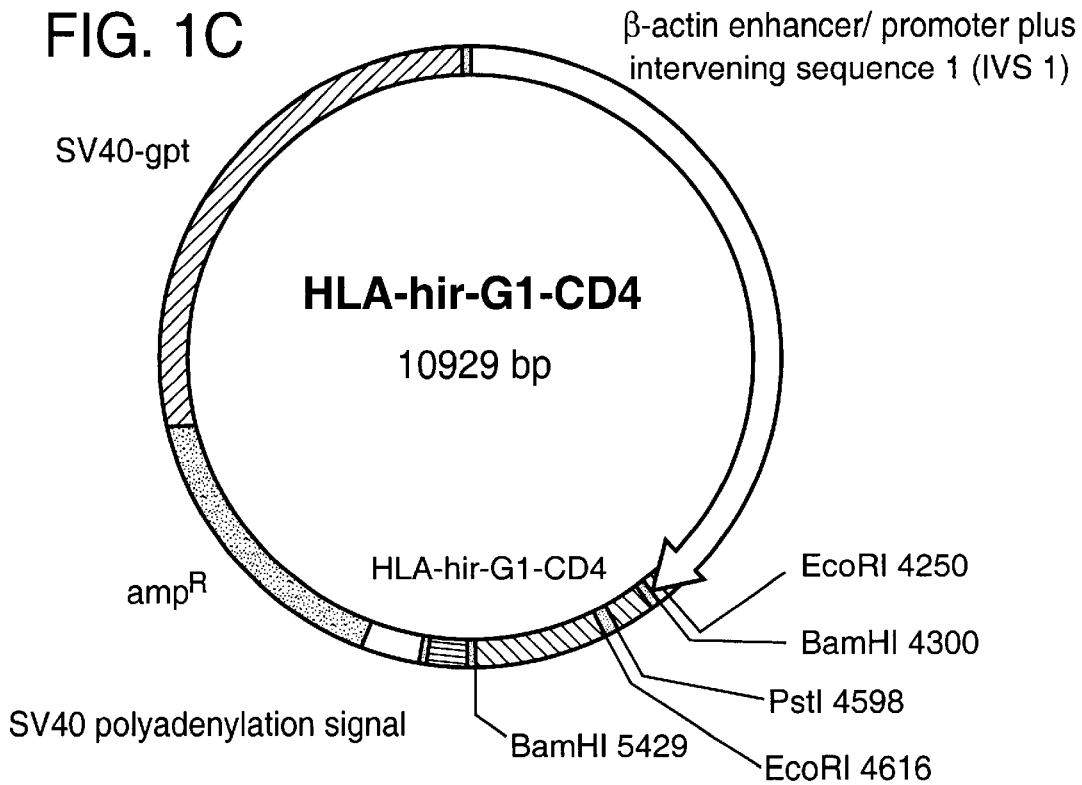
FIG. 1 shows maps of hirudin-CD4 chimeric proteins and constructs according to the invention. (A) HLA-hirudin-CD4 constructs with glycine linkers. (B) HLA-hirudin-CD4 construct with human P-selectin C-terminal, with the specific targeting sequence underlined. Transmembrane (TM), stop transfer (ST), and cytoplasmic (C) regions of CD4 are indicated.

1. Hirudin Fused with HLA Class I Signal Peptide and Linked to Domains 3 and 4 of Human CD4 is Tethered to the Cell Membrane To express heterologous hirudin constructs in mammalian cells, the cDNA for the membrane-targeting signal peptide leader sequence from human HLA class I A2.1, amino acids −1 to −24 (Holmes, 1987), was fused to hirudin variant 1 (Dodt, 1984) using PCR with overlapping extension (FIG. 1).

The HLA A2.1 leader sequence was amplified using primers:

5'-cagtgtcgacggatccatggccgtcatggcgccccga-3' [hla-1] <SEQ ID 1>

(introducing SalI and BamHI restriction sites) and:

5'-gtcagtgtaaacaaccgcccaggtctgggtcagg-3' <SEQ ID 2>

The hirudin sequence was amplified using primers:

5'-acccagacctgggcggttgtttacactgactgcacc-3' and <SEQ ID 3>

5'-gacgctgcagaattcttgcaggtattcttccgggatt-3' [hir-3] <SEQ ID 4>

(introducing distal EcoRI and PstI sites).

The resulting PCR products (108 and 228 bp) were purified by agarose gel electrophoresis and then used in a third PCR using flanking primers hla-1 and hir-3. The resulting PCR product (300 bp) was digested with SalI and BamHI and subcloned into pBluescript SK(+) (Stratagene).

An anchor consisting of a cDNA encoding for CD4 domains 3 and 4 (Maddon, 1985) in conjunction with the stop transfer sequence (ST), transmembrane and cytoplasmic domains of CD4 ($CD4_{166-435}$) was added to the HLA-hirudin cassette.

To ensure that hirudin stayed mobile and active when linked by its C-terminal to the CD4 anchor, however, 3 different glycine linker lengths were made (designated G1 to G3—FIG. 1A):

for glycine linker 1 (G1; GGSGG), the oligonucleotide pair consisted of 5'-aattaggaggttctggaggctgca-3' <SEQ ID 5> (containing a mutated EcoRI recognition sequence and a PstI site) and 5'-gcctccagaacctcct-3' <SEQ ID 6>;

glycine linkers 2 (G2) and 3 (G3) consisted of the core sequence (GGSGG) repeated two or three times, respectively.

These linkers were introduced into the 3' end of the HLA-hirudin fragment.

The glycine linker oligonucleotides were annealed and each ligated into the EcoRI/PstI site of plasmids containing the HLA-hirudin cassette, prior to the insertion of the CD4 anchor.

$CD4_{166-435}$ was amplified using primers:

5'-tgtctgcaggaaccagaagaaggtggaattca-3' <SEQ ID 7> (introducing PstI and EcoRI sites) and:

5'-gtgggatccgcctggcctcgtgcctcaa-3' <SEQ ID 8> (containing a distal BamHI).

The resulting PCR product was cloned into pbluescript and sequenced. In $CD4_{166-435}$, $V^{328}$ was found to be mutated to $A^{328}$. The PstI/BamHI CD4 fragment was subcloned into HLA-hirudin-G1, -G2, & -G3 plasmids, and these constructs were verified by DNA sequence analysis.

Figure 1D:
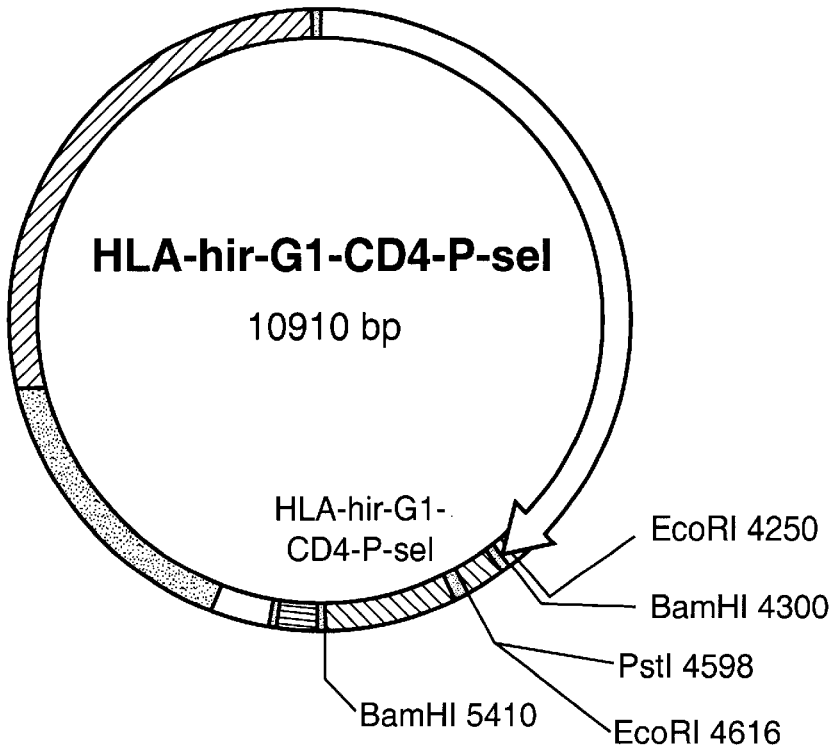
Figure 2A:
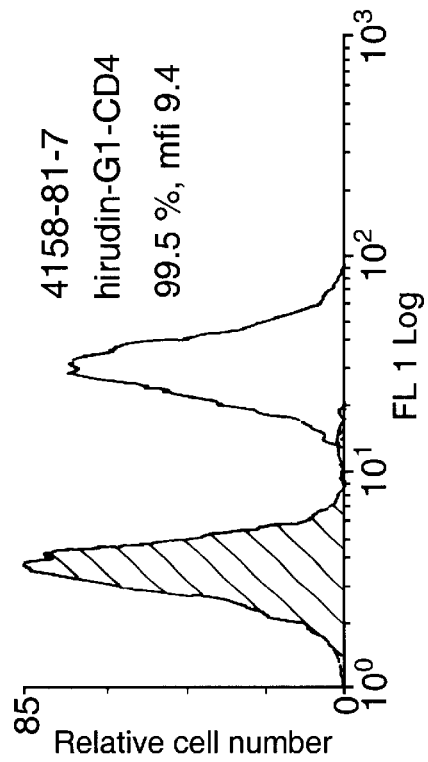
FIG. 2 shows FACS profiles for HLA-hirudin-CD4 constructs expressed in DAP.3 fibroblasts.
Figure 2B:
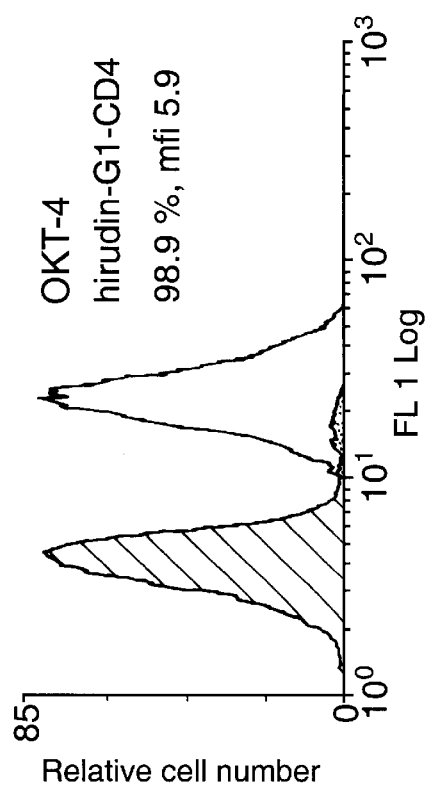
Figure 2C:
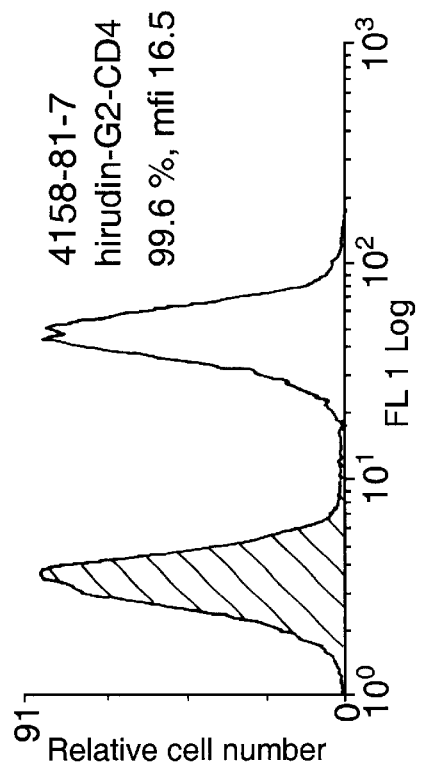
Figure 2D:
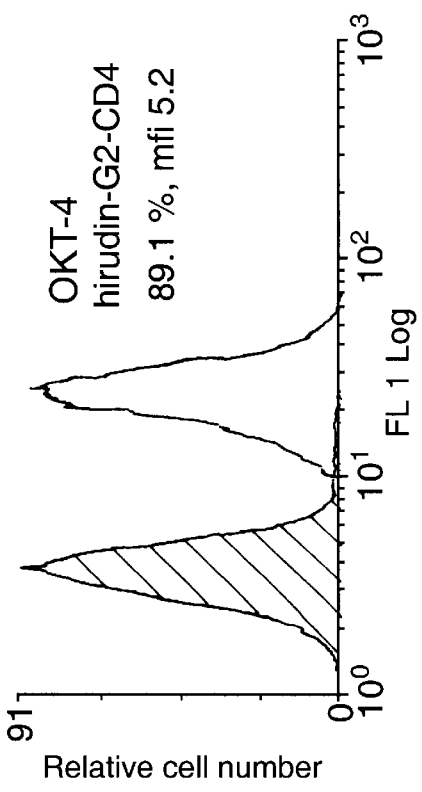
Figure 2F:
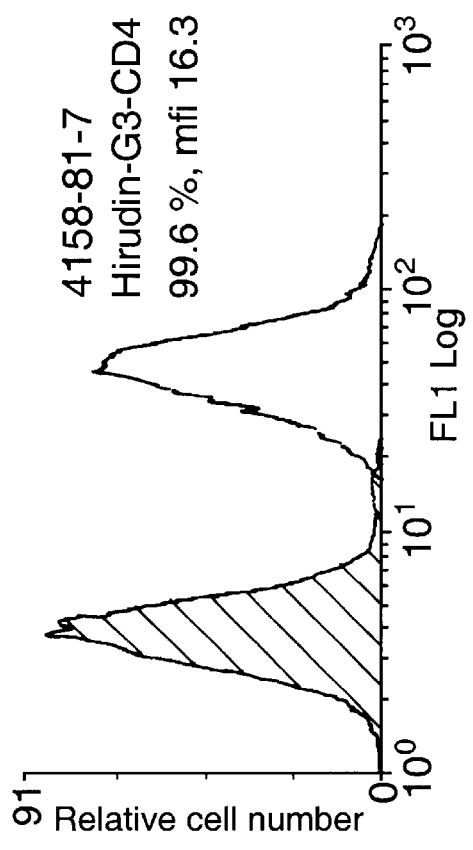
Figure 2E:
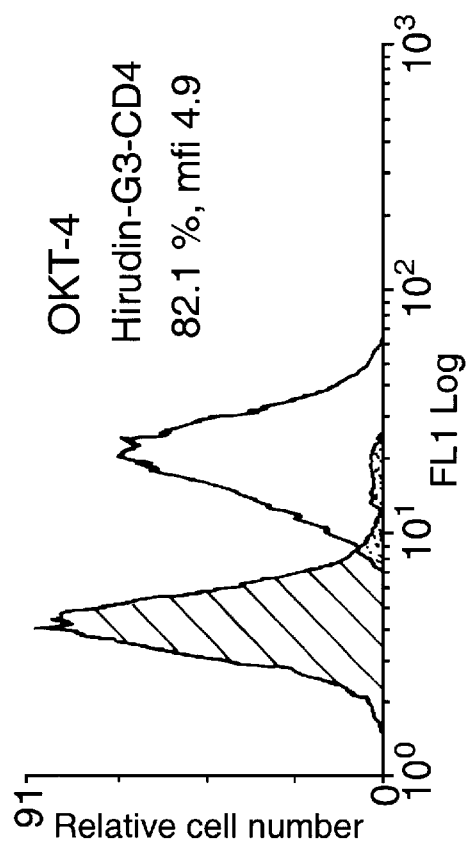
Figure 3B:
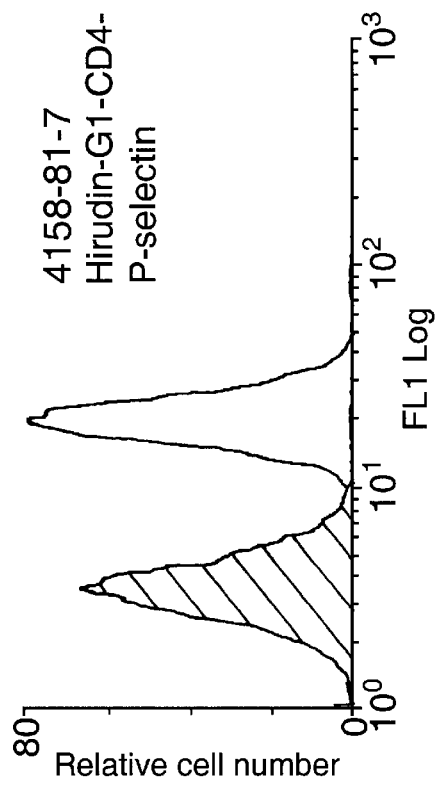
FIG. 3 shows FACS profiles for HLA-hirudin-CD4-P-selectin cDNA constructs expressed in CHO-K1.
Figure 3D:
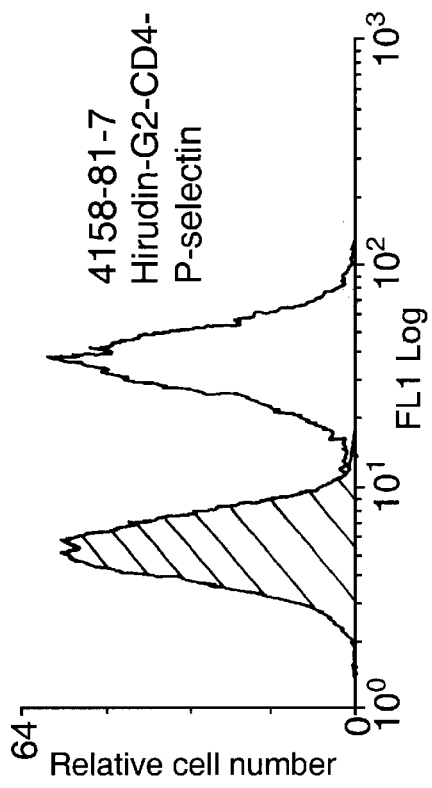
Figure 3A:
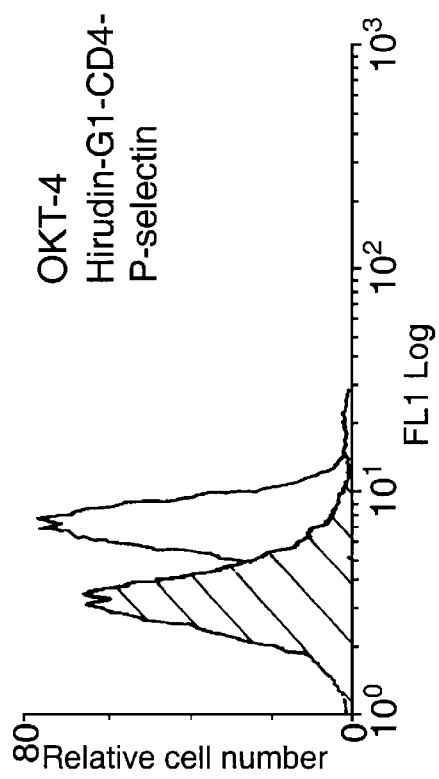
Figure 3C:
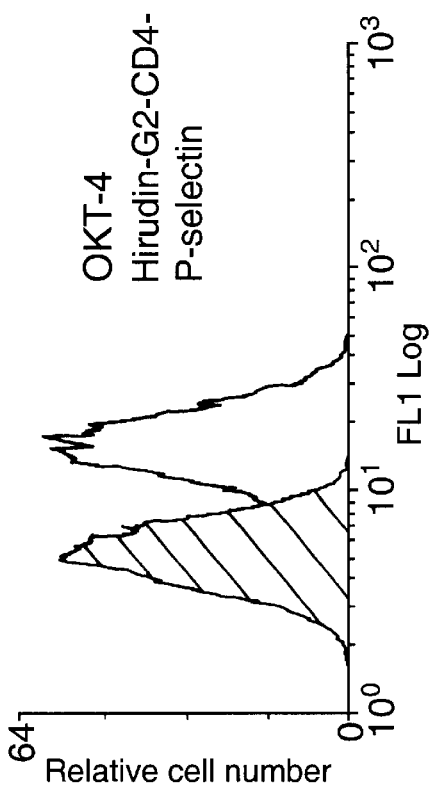
Figure 3E:
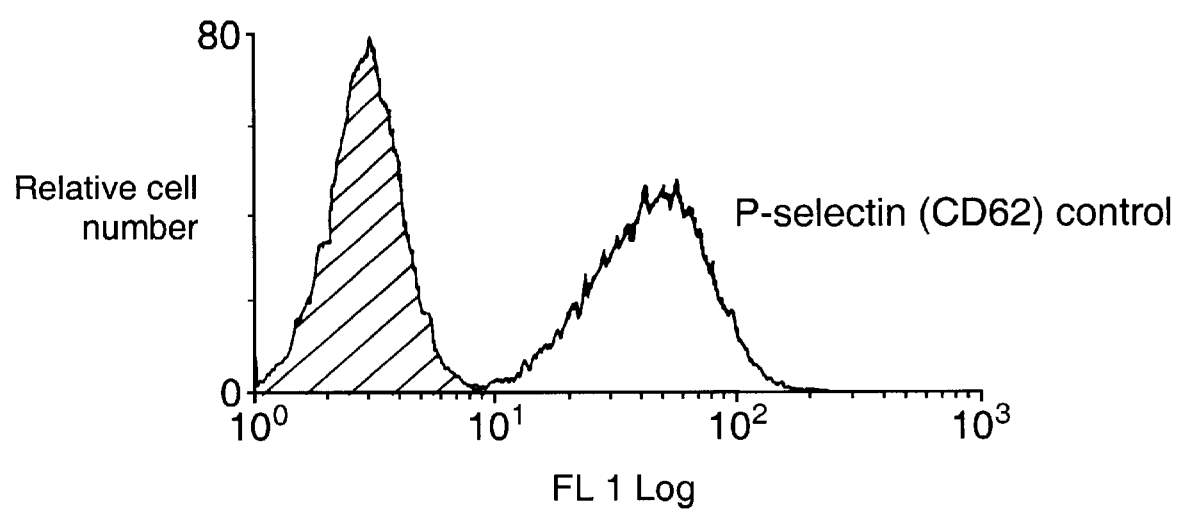

Each of the three cDNA constructs were subcloned into the BamHI site of the mammalian expression vector pHβActpr-1gpt (Gunning, 1987), containing the human β-actin enhancer and promoter region in conjunction with an SV40 enhancer element driving the gpt resistance gene, allowing the selection of clones in the presence of mycophenolic acid (FIGS. 1C & 1D). The orientation of the final constructs was verified by restriction endonuclease mapping.

Vectors containing the individual HLA-hirudin-G1/2/3-CD4 constructs were transfected into mouse fibroblast cell line DAP.3 (Marguelies, 1983) with calcium-phosphate according to standard protocols. After 18 hours growth in DMEM medium (Gibco) supplemented with 5% fetal calf serum, ampicillin, streptomycin, and glutamine, cells were glycerol treated for 30 seconds. Cells were then washed twice with phosphate buffered saline (PBS), and new medium including xanthine, hypoxanthine, and mycophenolic acid to a final concentration 12 µg/ml, was added.

For a negative control, DAP.3 cells transfected with a human class II construct expressing HLA-DR (cell line 531) (Lechler, 1988) grown in identical mycophenolic acid-containing culture medium.

Surviving clones were tested for hirudin and CD4 expression by FACS using murine monoclonal antibodies 4158-81-7 (Schlaeppi, 1991) and OKT-4 (Reinherz, 1979) respectively. $10^5$ cells were stained with the murine antibodies for 30 minutes on ice and a FITC-conjugated sheep anti-mouse polyclonal antibody was added as a secondary layer.

As shown in FIG. 2, these hirudin-CD4 constructs were well expressed at the cell surface of DAP.3. No significant difference in expression levels was detected between hirudin-CD4 with the three different glycine linker lengths.

Therefore anticoagulant polypeptides can be stably expressed on the cell surface.

2. Hirudin-CD4 with a Targeting Sequence from the C-terminal of P-selectin is Expressed at the Cell Surface of CHO-K1

In addition to the HLA-hirudin-G1/2/3-CD4 constructs, two more constructs were synthesised with targeting sequences derived from human P-selectin (FIG. 1B). The transmembrane region from CD4 was used for these constructs, while the stop transfer sequence and C-terminal were replaced with the corresponding sequences from P-selectin (Johnston, 1989).

To fuse CD4 domains 3 and 4 plus the transmembrane region ($CD4_{166-395}$) with the stop transfer sequence and cytoplasmic regions 1 and 2 of human P-selectin ($P-sel_{754-789}$) (McEver 1989), PCR with overlapping extension was performed. For amplification of the CD4 part of the molecule, primers:

5'-tgtctgcaggaaccagaagaaggtggaattca-3' [CD4-5] <SEQ ID 7>

(introducing PstI and EcoRI restriction sites) and:

5'-gtctgaaacgctttctgaagaagatgcctagcccaatgaaaagcaggaggccg-3' <SEQ ID 9> were used. In parallel, to amplify the C-terminal region of P-selectin, primers:

5'-tgggctaggcatcttcttcagaaagcgtttcagacaaaaaga-3' and <SEQ ID 10>

5'-gaccaggatccggacaggtctctta-3' [P-selN3] <SEQ ID 11> (introducing a distal BamHI site) were used.

After purification of resulting PCR products from agarose gels, a third PCR was run using the flanking primers CD4-5 and P-selN3. The resulting PCR product (832 bp) was digested with PstI and BamHI, subcloned into pBluescript, and sequenced. Thereafter, the CD4-P-sel fragment ($CD_{166-395}$-$P-sel_{754-789}$) was excised with PstI/BamHI and subcloned into plasmids containing HLA-hirudin-G1 or -G2.

The final HLA-hirudin-G1/G2-CD4-P-selectin constructs were subcloned into the BamHI site of pHβActpr-1gpt and transfected into CHO-K1 cells (ATCC CCL61), grown in RPMI 1640 medium (Gibco) supplemented with 5% fetal calf serum, ampicillin, streptomycin, and glutamine.

Transfection was by electroporation according to standard protocols. Briefly, $5 \times 10^6$ cells were resuspended in 350 μl serum-free medium and transferred to a 1 ml electroporation cuvette with a 0.4 cm space between electrodes (Bio-Rad). After addition of 10 μg plasmid DNA in 150 μl, samples were gently shaken and kept on ice. Cells were subjected to electroporation at infinite resistance, 960 μF and 350 V in a Gene Pulser apparatus (Bio-Rad). The day after electroporation. cells were washed twice with PBS and new medium including mycophenolic acid, xanthine, and hypoxanthine was added.

Recently it was shown that when CHO-K1 cells were transfected with P-selectin cDNA, P-selectin protein was not accumulated intracellularly, but was expressed at the cell surface (Disdier, 1992). In the CHO-K1 transfectants produced above, both hirudin-G1-CD4-P-selectin and hirudin-G2-CD4-P-selectin were expressed at the surface as judged by staining with OKT-4 and 4158-81-7 monoclonals (FIG. 3). The negative control used was a CHO-K1 cell line expressing TFPI fused to CD4 domains 3 and 4 (TFPI-$CD4_{166-435}$), grown in the same mycophenolic acid-containing medium.

As a positive control, CHO-K1 cells were transfected with full length human P-selectin (Johnston, 1989), which was subcloned as a 3142 bp SalI fragment into pHβActpr-1neo containing an SV40-driven neomycin (G418) resistance gene. These cells were treated with 400 μg/ml G418 and after 2 weeks individual clones were picked with cotton swabs and transferred to 12-well plates. Surviving clones were analysed for hirudin and CD4 expression using 4158-81-7 at 10 μg/ml and an undiluted OKT-4 hybridoma supernatant.

Human P-selectin was detected by anti-CD62 mAb (Becton Dickinson), according to the manufacturer's recommendations. A similar FACS profile as with hirudin-CD4-P-selectin was observed for these CD62-labelled cells (FIG. 3E), confirming that CHO-K1 cells express P-selectin at the plasma membrane.

Thus, chimeric proteins comprising the P-selectin targeting sequence remain functional when expressed at the cell surface.

3. Hirudin Anchored to the Cell Surface Binds Thrombin as Detected with Specific Antibodies To test whether hirudin tethered in this way to the cell surface retains its thrombin binding activity, the following binding assay was used.

Stably transfected cells were grown in T75 culture flasks for 36 hours before each experiment. DAP.3 cells were detached using a cell scraper, whilst CHO-K1 cells were detached from the plastic by treatment with PBS, 5 mM EDTA for 10 minutes at 37° C. After 4 washes with PBS containing 0.1% BSA (w/v), $2.5 \times 10^5$ cells in 150 μl were incubated for 1 hour at 37° C. with increasing concentrations of thrombin. The cells were washed four times with PBS containing 0.1% BSA and further incubated for 30 minutes on ice with rabbit anti-human prothrombin immunoglobulins (10 μg/ml in 100 μl) (Dakopatts). After two further washes, cells were incubated for 30 minutes with FITC-conjugated swine anti-rabbit immunoglobulins (Dakopatts). Finally, transfectants were washed three times and analysed by flow cytometry.

As shown in FIG. 4, hirudin expressed at the cell surface retains the ability to bind thrombin and glycine linker length did not influence thrombin binding.

Figure 4D:
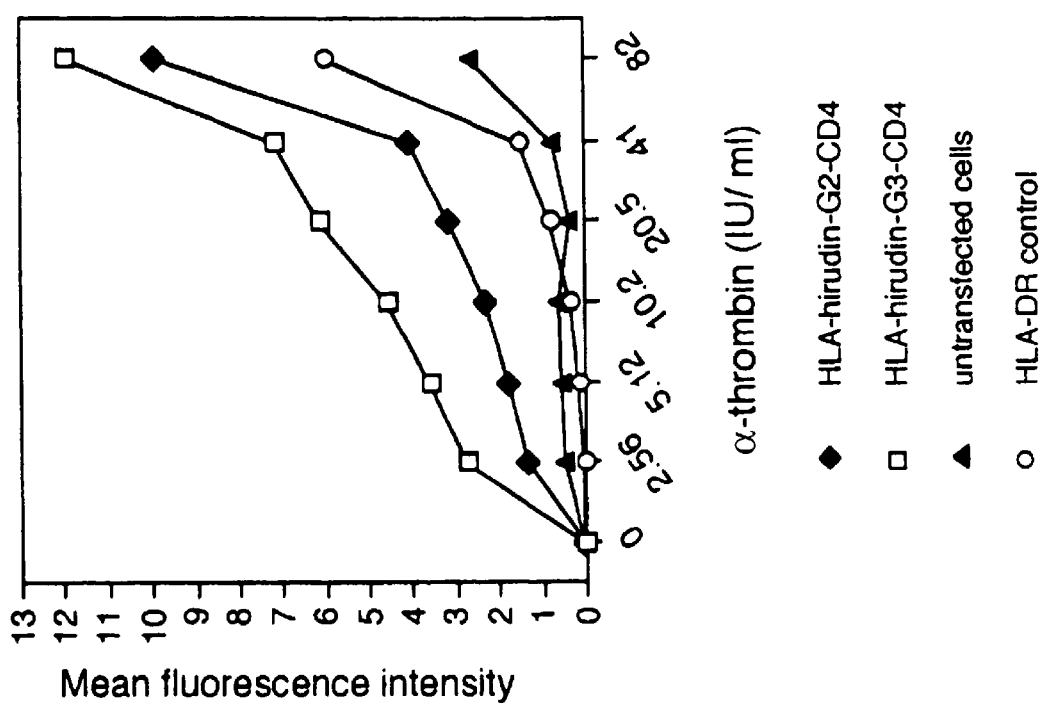
FIG. 4 shows that hirudin-CD4 expressing fibroblasts bind thrombin.
Figure 4C:
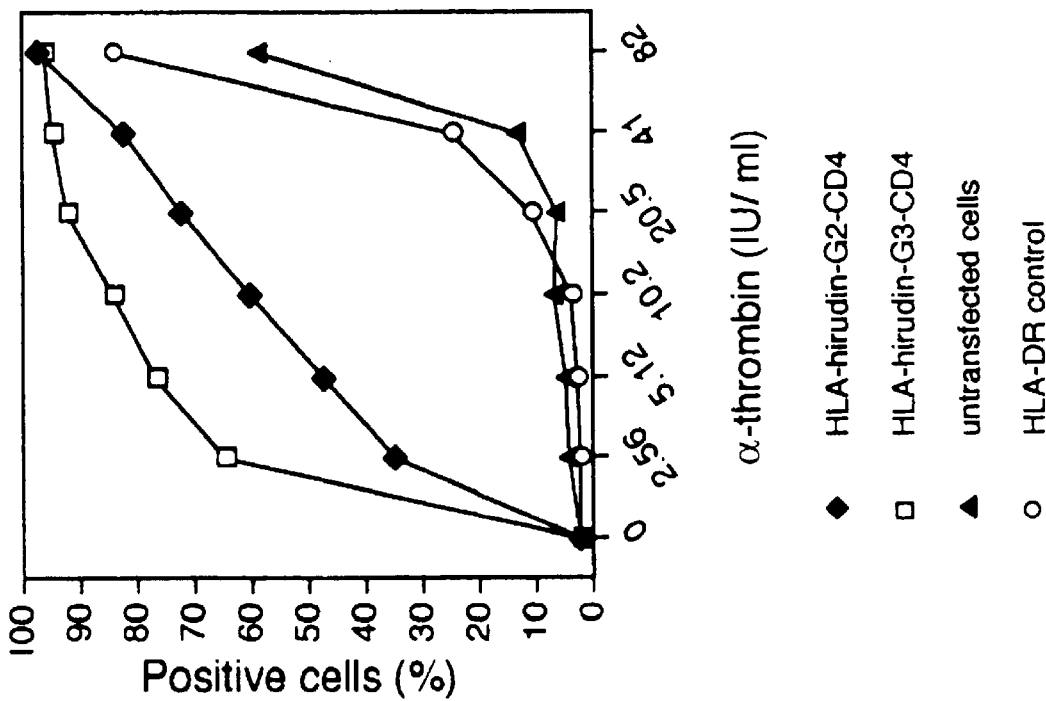

To assess the amount of thrombin needed to saturate the hirudin-CD4 expressing cells, two clones were incubated with thrombin up to 82 U/ml. When percentage positive cells was analysed, transfectants were saturated at 41 U/ml thrombin (FIG. 4C). According to the mean fluorescence intensities (mfi), however, cells were not saturated even at 82 U/ml (FIG. 4D). At these high experimental thrombin concentrations the background binding to control cells expressing HLA-DR increased significantly.

To elucidate the specificity of thrombin binding to hirudin-CD4 further, blocking experiments were carried out. DAP.3 HLA-hirudin-G3-CD4 transfectants were pre-incubated on ice for 30 minutes with 10 μg/ml anti-hirudin mAb or appropriate controls (mouse IgG1 and IgG2a, Dakopatts) for 30 minutes on ice, and washed twice in PBS containing 0.1% BSA before incubating with thrombin for 1 hour at 37° C. as above. Thrombin binding was analysed as above.

Pre-incubation with 4158-81-7 inhibited specific thrombin binding to hirudin-CD4 (FIG. 5A). Thrombin binding by hirudin-CD4 was demonstrated by incubation with thrombin and comparing labelling with mAb 4107-76-1 (Schlaeppi, 1991) and anti-prothrombin immunoglobulins. 4107-76-1 is directed against the hirudin-thrombin complex and detects neither hirudin without thrombin nor thrombin bound to endogenous thrombin receptors. As shown in FIG. 5B, thrombin binding detected with 4107-76-1 paralleled the binding observed with the anti-prothrombin immunoglobulin fraction.

Thus hirudin expressed on the surface of DAP.3 cells retains specific thrombin binding.

Immortalised porcine epithelial cells (IPEC) were transfected with hirudin-CD4 in the same way. As shown in FIG. 15A, only the transfected cells bound thrombin, and this was blocked by the 4158-81-7 in a dose-dependent manner (FIG.

15B). A human plasma recalcification test system was used for further investigation of the functional effect of expressing surface-tethered hirudin on IPEC. As shown in FIG. 15C, untransfected IPEC shortened the clotting time of recalcified plasma to approximately 170 seconds, compared with a control clotting time 370s in the absence of cells. Preincubation with IL-1, which induces TF expression, further reduced the clotting time to below 100s. In contrast, clotting times for transfected IPEC were prolonged, even after preincubation with IL-1-induced TF expression. Incubation with 4158-81-7 reduced the anticoagulant effect in a dose-dependent manner, indicating that the effect was due to the presence of cell-surface hirudin (FIG. 15D).

Hirudin expressed on the surface of IPEC thus binds thrombin and also inhibits the clotting of human plasma.

4. Hirudin-CD4-P-selectin Expressed by CHO-K1 Cells Binds Thrombin

To investigate whether hirudin-CD4-P-selectin also binds thrombin when expressed at the surface of CHO-K1 cells, these cells were incubated with thrombin for 1 hour at 37° C. After staining with anti-prothrombin immunoglobulins and addition of a second FITC-labelled antibody layer, cells were analysed by flow cytometry.

Figure 6B:
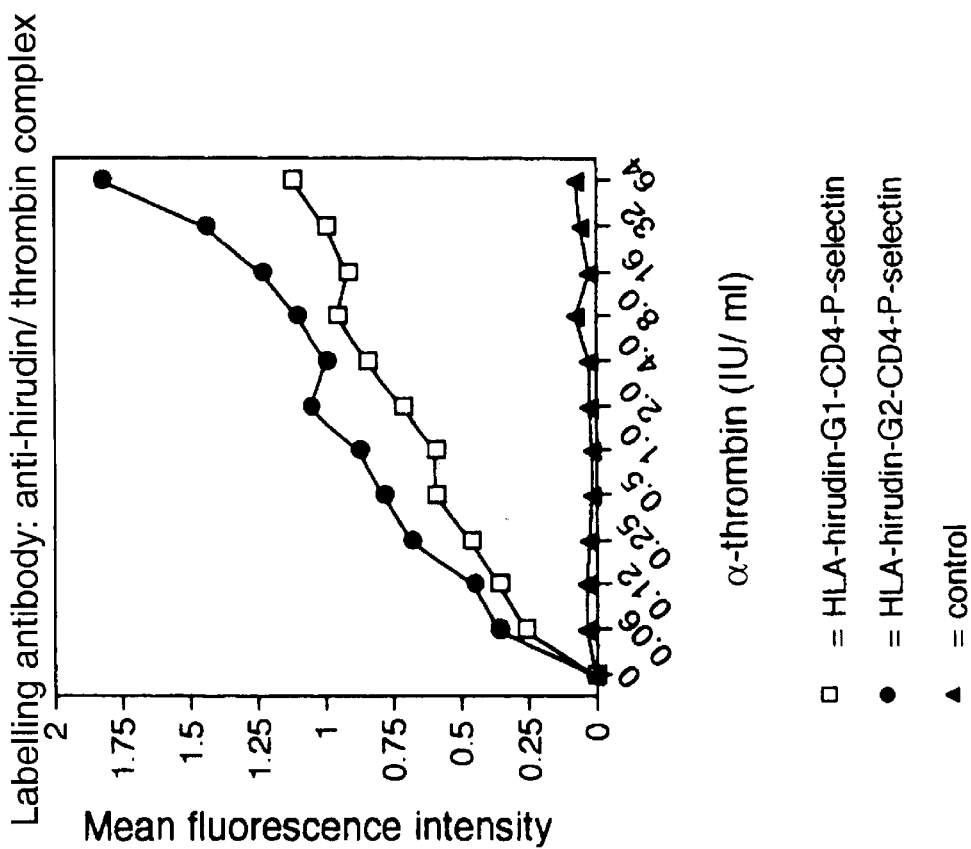
FIG. 6 shows thrombin binding to CHO-K1 cells transfected with HLA-hirudin constructs.
Figure 6A:
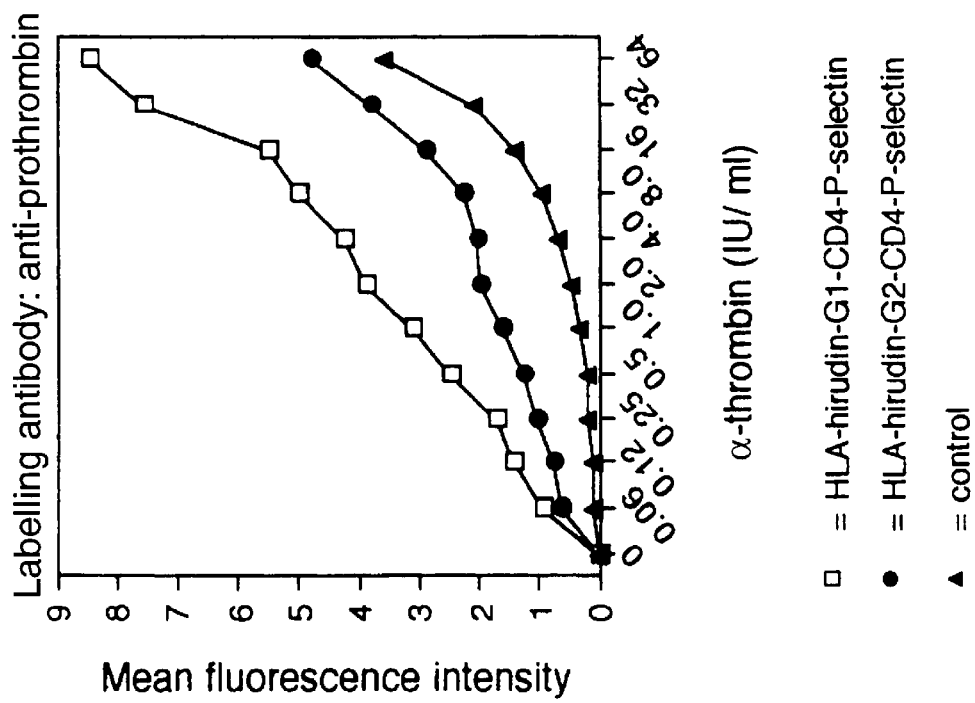

A distinct binding profile was detected, as shown in FIG. 6A. With anti-prothrombin immunoglobulins, background thrombin binding to CHO-K1 cells expressing an irrelevant protein linked to CD4 was detectable after incubation with fairly low concentrations of thrombin. However, specific thrombin binding to hirudin was verified by staining with the specific anti-hirudin/thrombin mAb 4107-76-1 (FIG. 6B). With this antibody, background binding by the control CHO-K1 cells was undetectable. It is also evident from FIG. 6 that clones expressing hirudin appeared to bind thrombin non-specifically to a different degree, implying that they had different expression levels of endogenous thrombin receptors. This variation in non-specific binding was confirmed with several other clones.

Figure 6D:
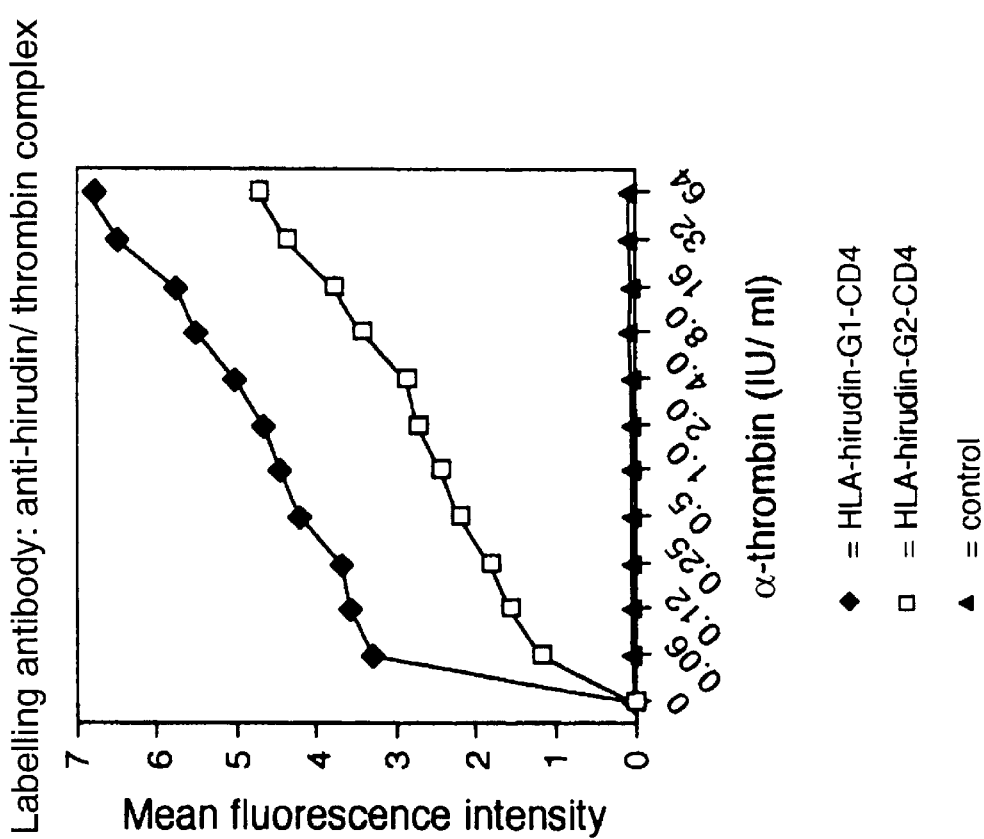
Figure 6C:
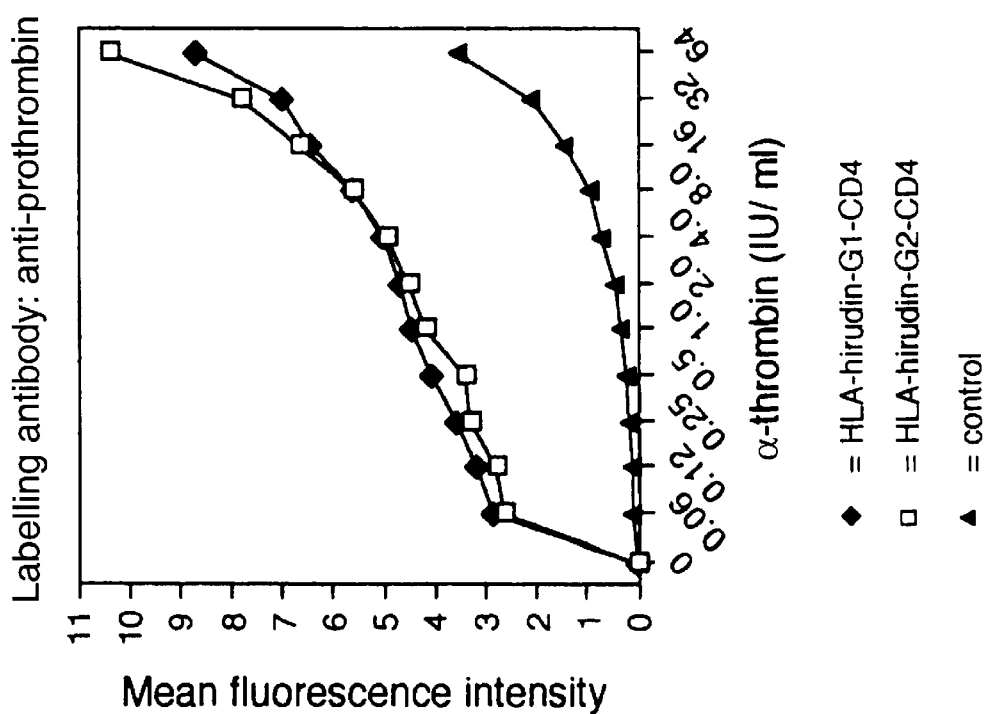

For comparison, results from two CHO-K1 transfectants expressing hirudin-G1-CD4 and hirudin-G2-CD4 (ie. no P-selectin sequence) are shown in FIGS. 6C and 6D. Except for a slightly increased thrombin binding due to better expressed chimeric proteins (higher mfi's), no major differences in binding profiles were detected compared to transfectants expressing hirudin linked to the CD4-P-selectin anchor.

5. Hirudin-CD4-P-selectin is Stored in Secretory Granules and can be Released on Activation To examine intracellular accumulation of hirudin and its route from secretory granules to the cell surface, a secretory murine pituitary cell line (D16/16) was transiently transfected with cDNA encoding either hirudin-CD4-P-selectin or hirudin-CD4. This cell line was chosen for two reasons. Firstly, these cells are known to express ACTH in specific storage granules, which are discharged at the cell surface on activation with phorbol esters. Secondly, endothelial cells (which would appear to be the ideal cell type to investigate intracellular targeting of the P-selectin construct) rapidly lose their Weibel-Palade storage granules during in vitro culture.

Figure 16A:
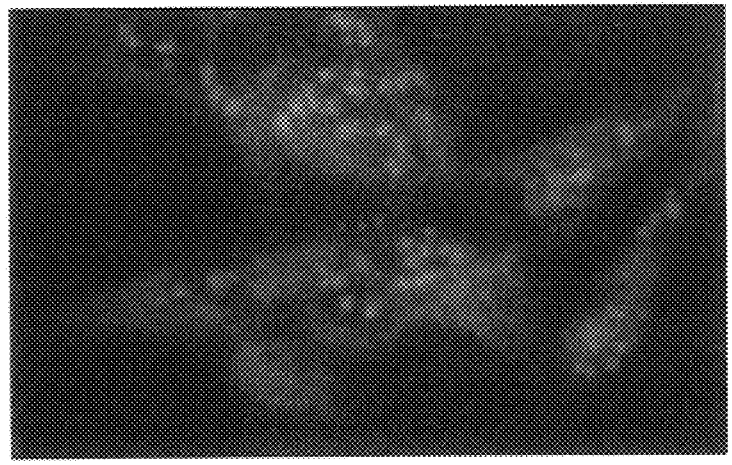
FIGS. 16A–F shows the distribution of ACTH and hirudin in D16/16 cells, as revealed by fluorescence.
Figure 16B:
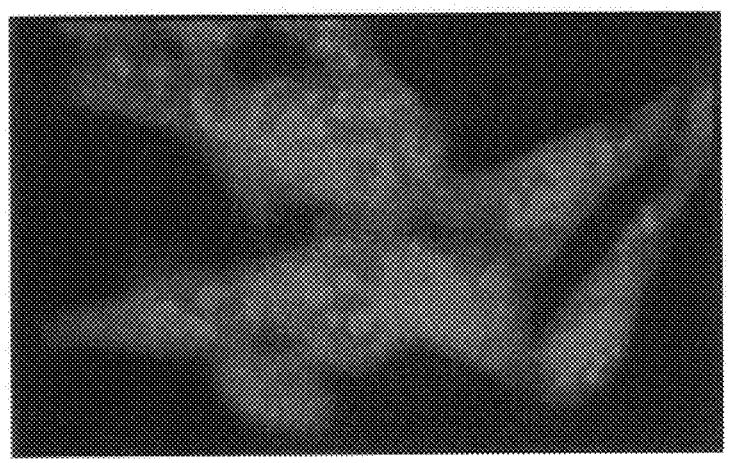
Figure 16C:
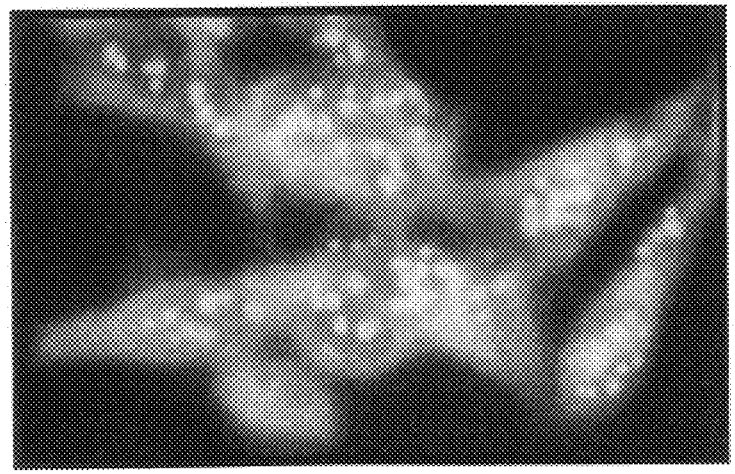

48 hours after transfection, D16/16 cells were stained with antibodies against hirudin and ACTH. In cells transfected with hirudin-CD4-P-selectin, hirudin was detected in granules evenly distributed in the cytoplasm (FIG. 16A). The same pattern of granule distribution was seen with ACTH-specific staining, implying co-localisation with hirudin (FIG. 16B). This was verified when both antibodies were used for staining (FIG. 16C).

Figure 16D:
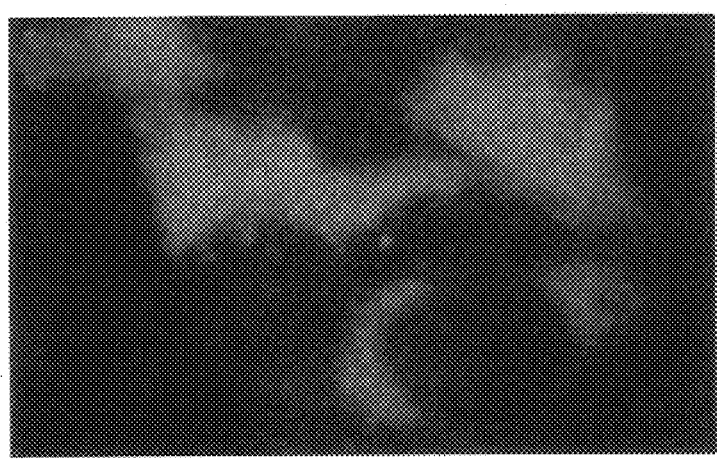
Figure 16E:
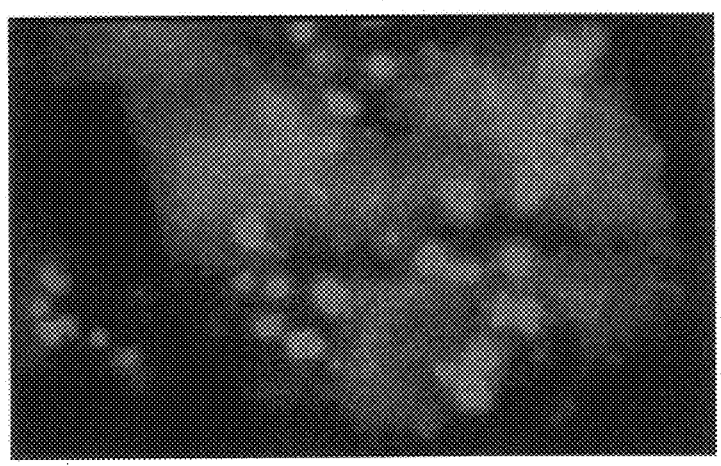
Figure 16F:
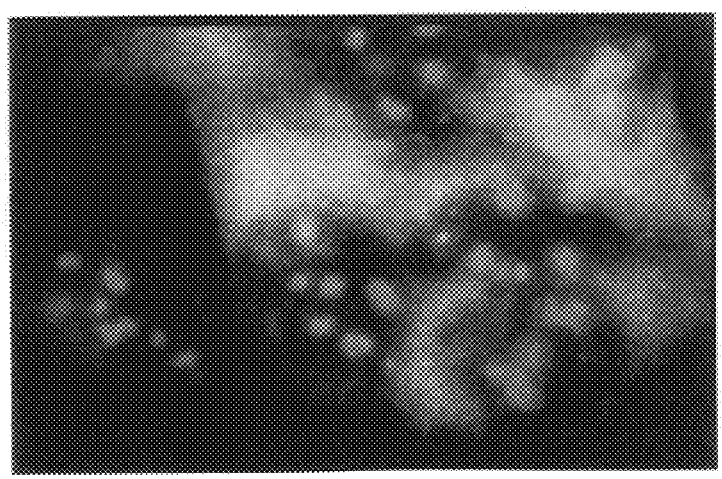

In contrast, D16/16 cells transfected with hirudin-CD4 did not accumulate hirudin in intracellular granules, but expressed high levels of hirudin at the cell surface (FIG. 16D). Dual staining (FIG. 16F) revealed only slight co-localisation of hirudin and ACTH.

Cells expressing hirudin-CD4-P-selectin were activated with phorbol ester PMA, and were analysed by flow cytometry. 4158-81-7 did not detect any hirudin at the cell-surface in unstimulated cells (FIG. 17A). After 30 minutes of PMA-stimulation, however, hirudin was detected at the cell-surface (FIG. 17B). Furthermore, activated D16/16 cells specifically bound to thrombin, unlike non-activated cells (FIG. 17C—stained with 4107-76-1).

Thus, by using the granule-containing pituitary cell line D16/16, it was clearly demonstrated that hirudin-CD4-P-selectin can be targeted to specific intracellular storage granules, and that functional chimeric molecules can be released and exposed at the cell surface upon activation.

6. The Interaction Between Thrombin and Hirudin-CD4 is Abolished when the Catalytic Site of Thrombin is Inactivated Specific thrombin binding to hirudin-CD4 with and without P-selectin targeting sequence was clear (FIGS. 4 and 6). To strengthen the specificity of the thrombin-hirudin interaction further, thrombin (210 nmol in 50 $\mu$l Tris-buffered saline (TBS), 0.1% BSA, pH 7.4) was pre-incubated for 1 hour at 37° C. with either:

- native full-length hirudin (Biopharm) at a 10-fold molar excess;
- D-Phe-Pro-Arg chloromethyl ketone dihydrochloride ("PPACK-HCl")(Calbiochem) at 100-fold molar excess; or
- a synthetic C-terminal hirudin dodecapeptide analog comprising hirudin residues 53–64, with sulfato-Tyr64 (American Diagnostica) at 100-fold molar excess.

The thrombin-dependent catalytic activity was analysed with a small chromogenic oligopeptide substrate (H-D-Phe-Pip-Arg-pNA•2HCl ("S-2238") (Quadratech).

To ascertain whether thrombin was inactivated by PPACK-HCl and hirudin, 5 $\mu$l of each reaction mixture were diluted with 95 ml TBS, 0.1% BSA and incubated with 50 $\mu$l 4 mM S-2238 for 10 minutes at 37° C.

As expected, no chromogenic conversion was observed with thrombin incubated with PPACK-HCl or hirudin as compared to thrombin incubated without inhibitor, whereas the dodecapeptide did not influence thrombin-dependent catalytic activity as measured by cleavage of S-2238.

Figure 7B:
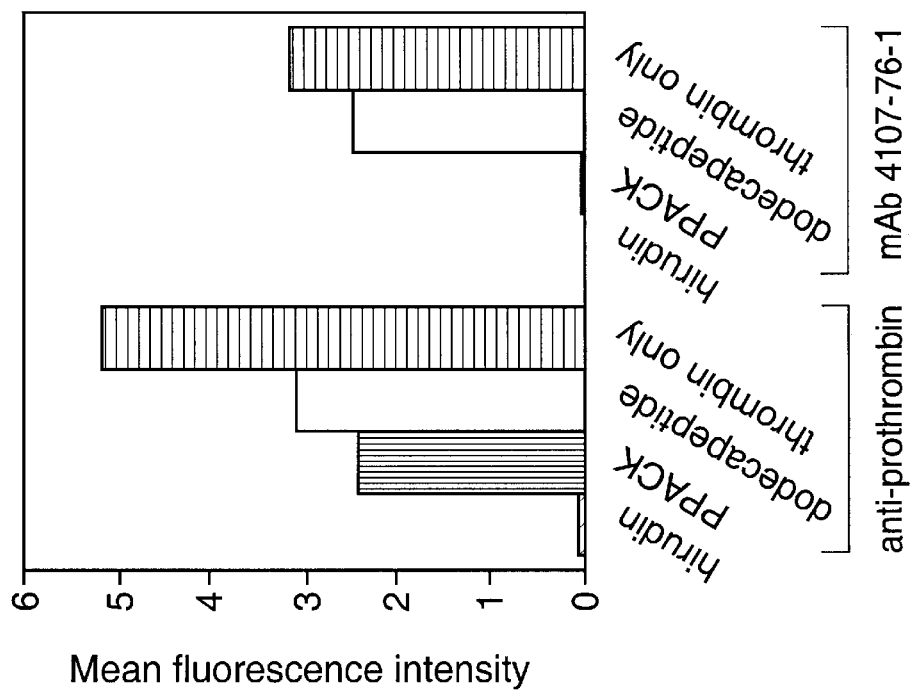
FIG. 7 shows that inactivation of thrombin abolishes thrombin binding to hirudin-CD4 at the cell surface. Cells expressing hirudin-G2-CD4 were incubated with thrombin or inactivated thrombin and stained for thrombin binding with anti-prothrombin or anti-thrombin-hirudin antibodies.
Figure 7A:
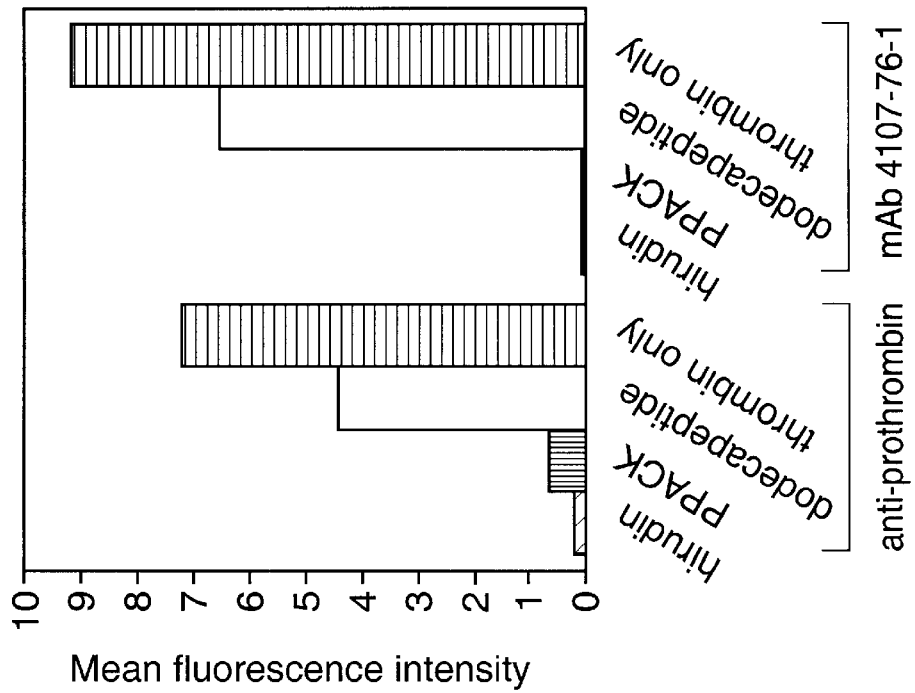

The three different preparations were added to transfectants expressing hirudin tethered to the cell surface. Using the procedure described above, thrombin binding was investigated with the anti-prothrombin or anti-hirudin-thrombin antibodies. As can be seen in FIG. 7A, thrombin inactivated with hirudin or PPACK-HCl was not bound by hirudin expressed at the cell surface of DAP.3. In addition, only a partial thrombin-dodecapeptide complex binding was observed. In contrast to DAP.3 transfectants, CHO-K1 cells displayed a relatively high thrombin-PPACK-HCl binding (FIG. 7B). This interaction was found to be unspecific as illustrated with the anti-hirudin-thrombin mAb 4107-76-1. No specific thrombin-PPACK-HCl-hirudin binding was detected.

This confirms that hirudin tethered to the cell surface specifically and strongly binds thrombin at its catalytic site.

Figure 8A:
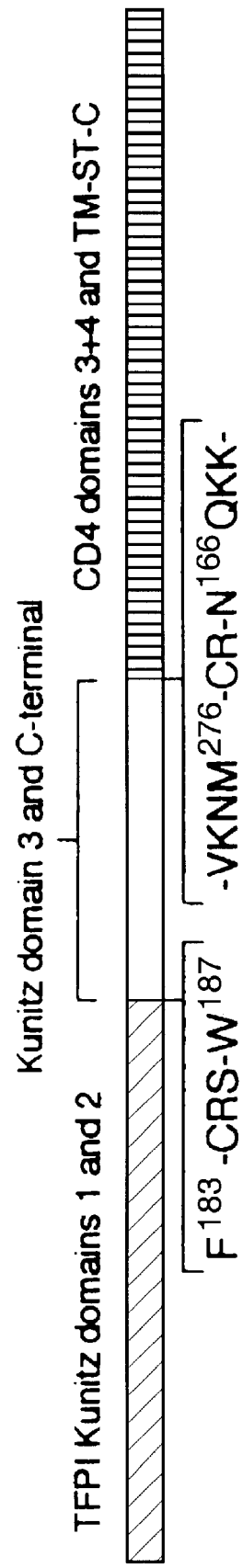
FIG. 8 shows maps of TFPI-CD4 chimeric proteins and constructs according to the invention.
Figure 8B:
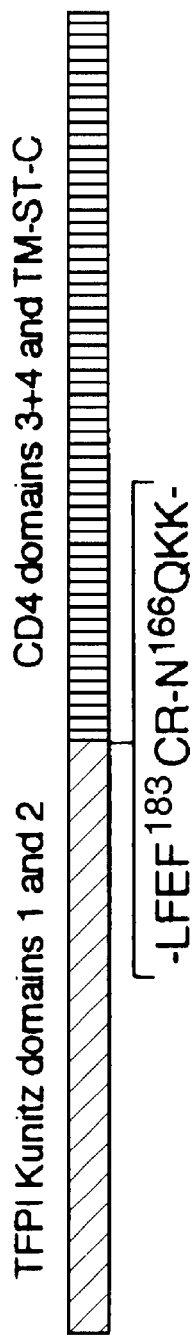
Figure 8C:
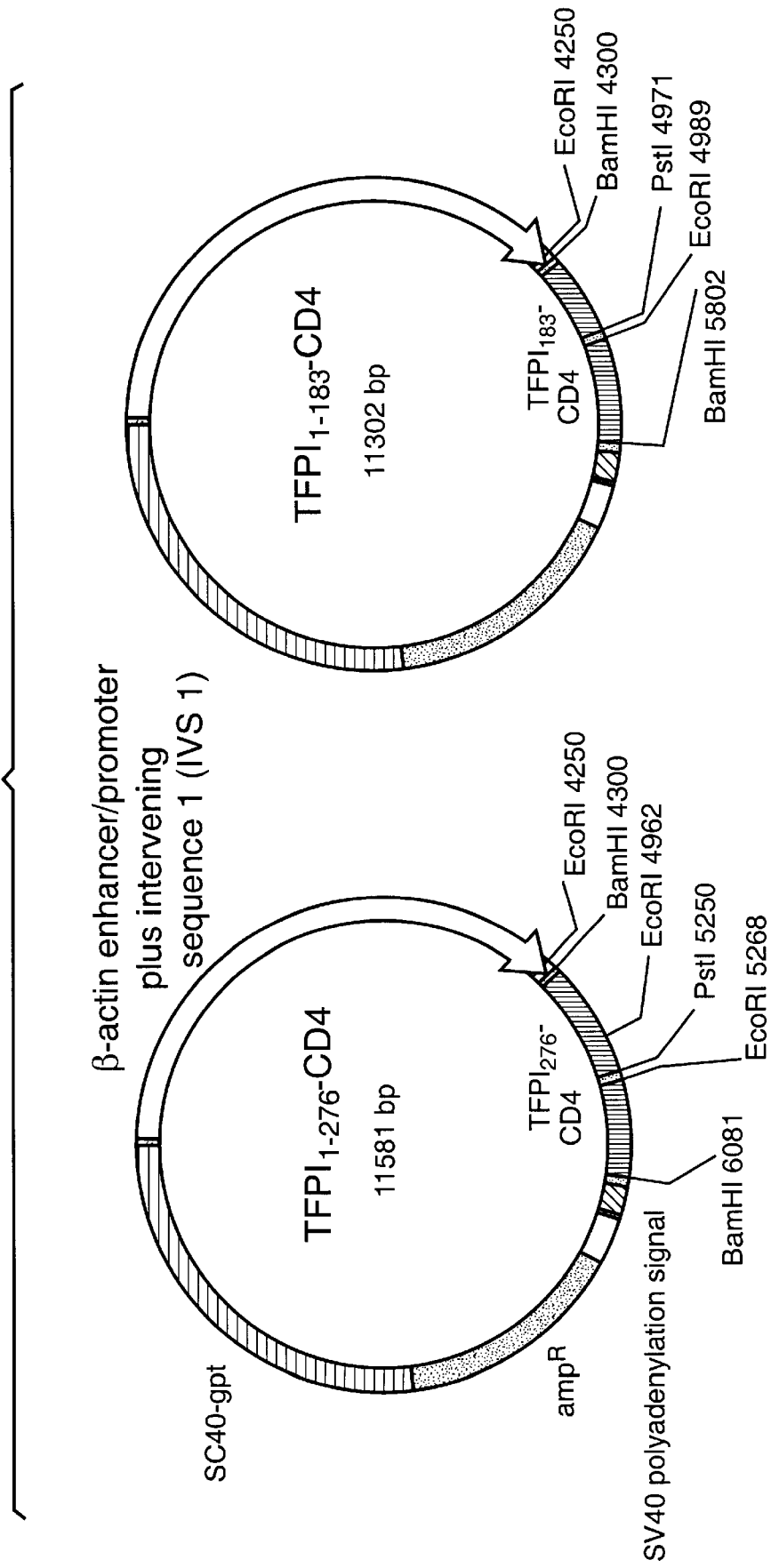
Figure 9A:
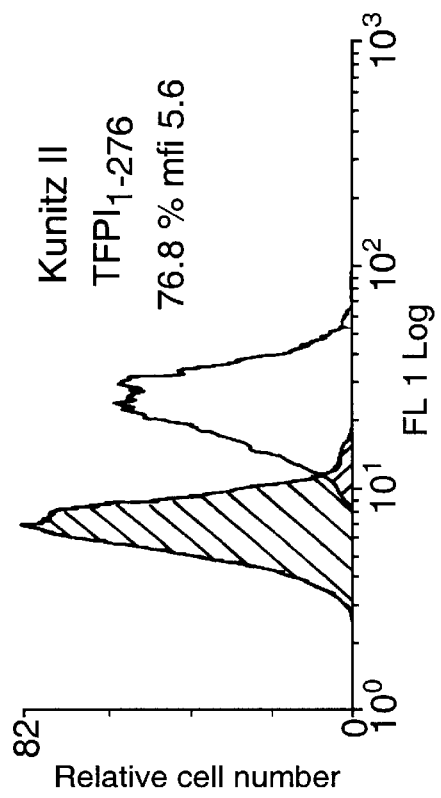
FIG. 9 shows flow cytometry profiles of DAP.3 cells expressing TFPI tethered to the cell surface.
Figure 9B:
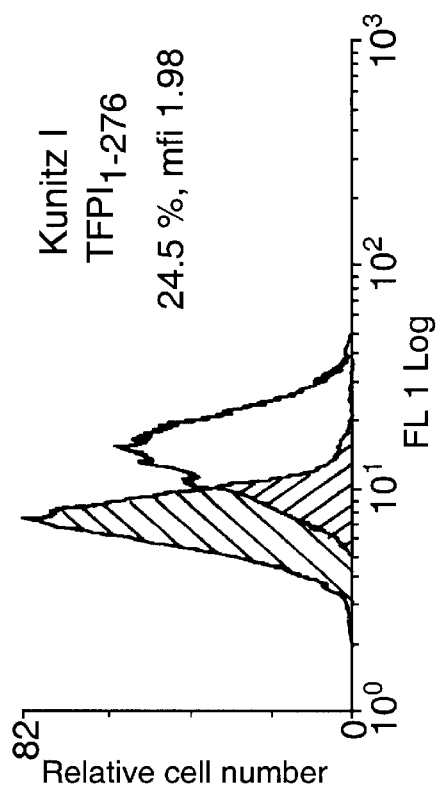
Figure 9D:
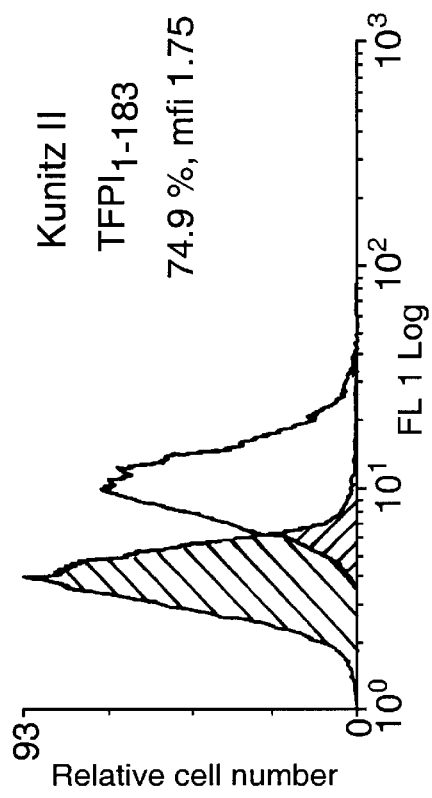
Figure 9E:
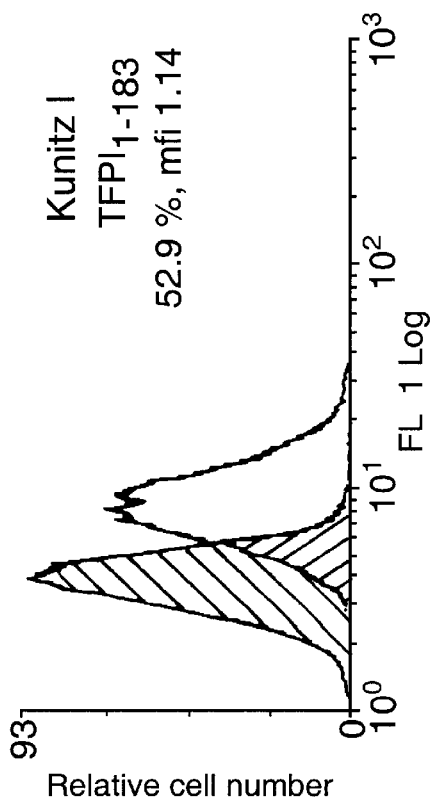
Figure 9C:
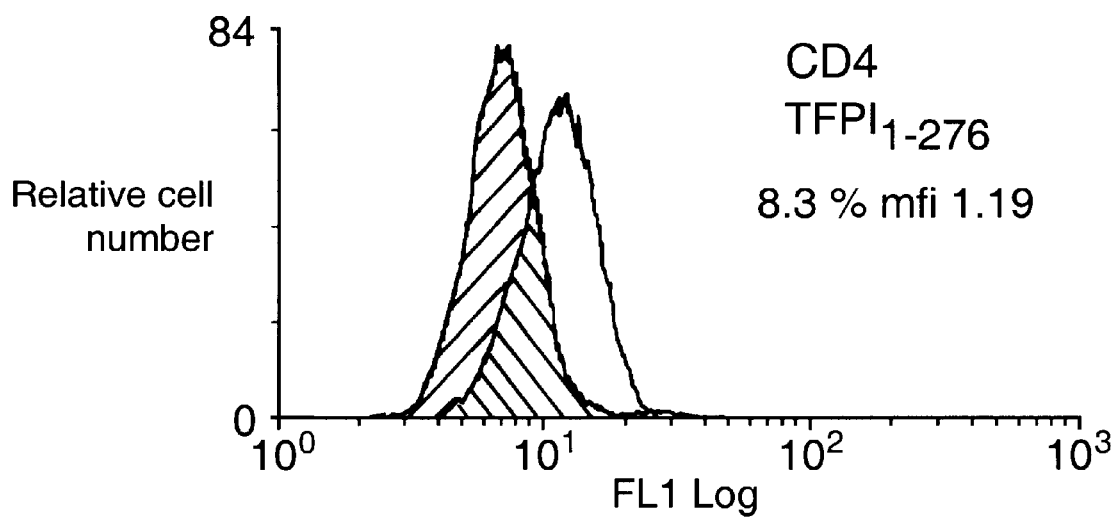
Figure 9F:
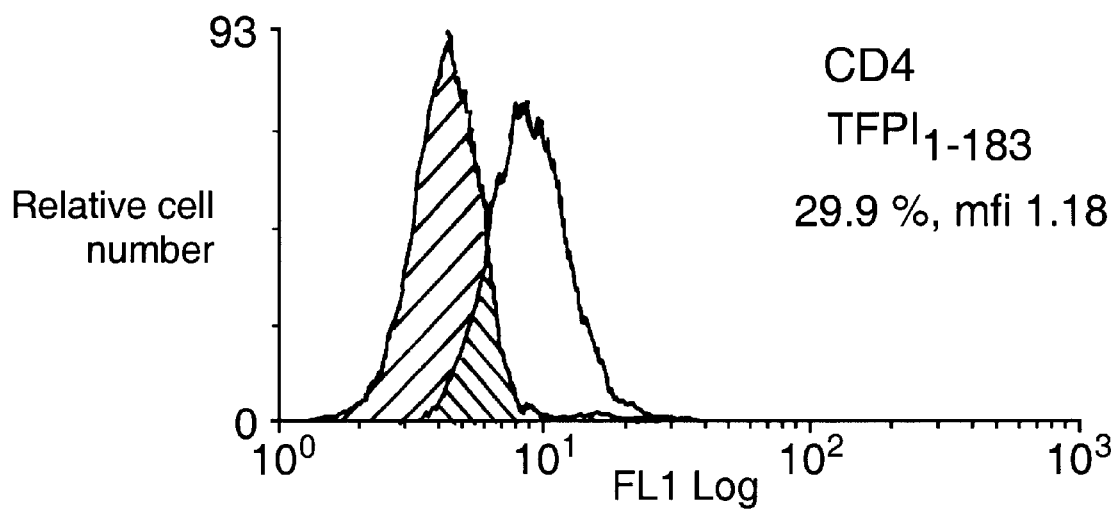
Figure 10:
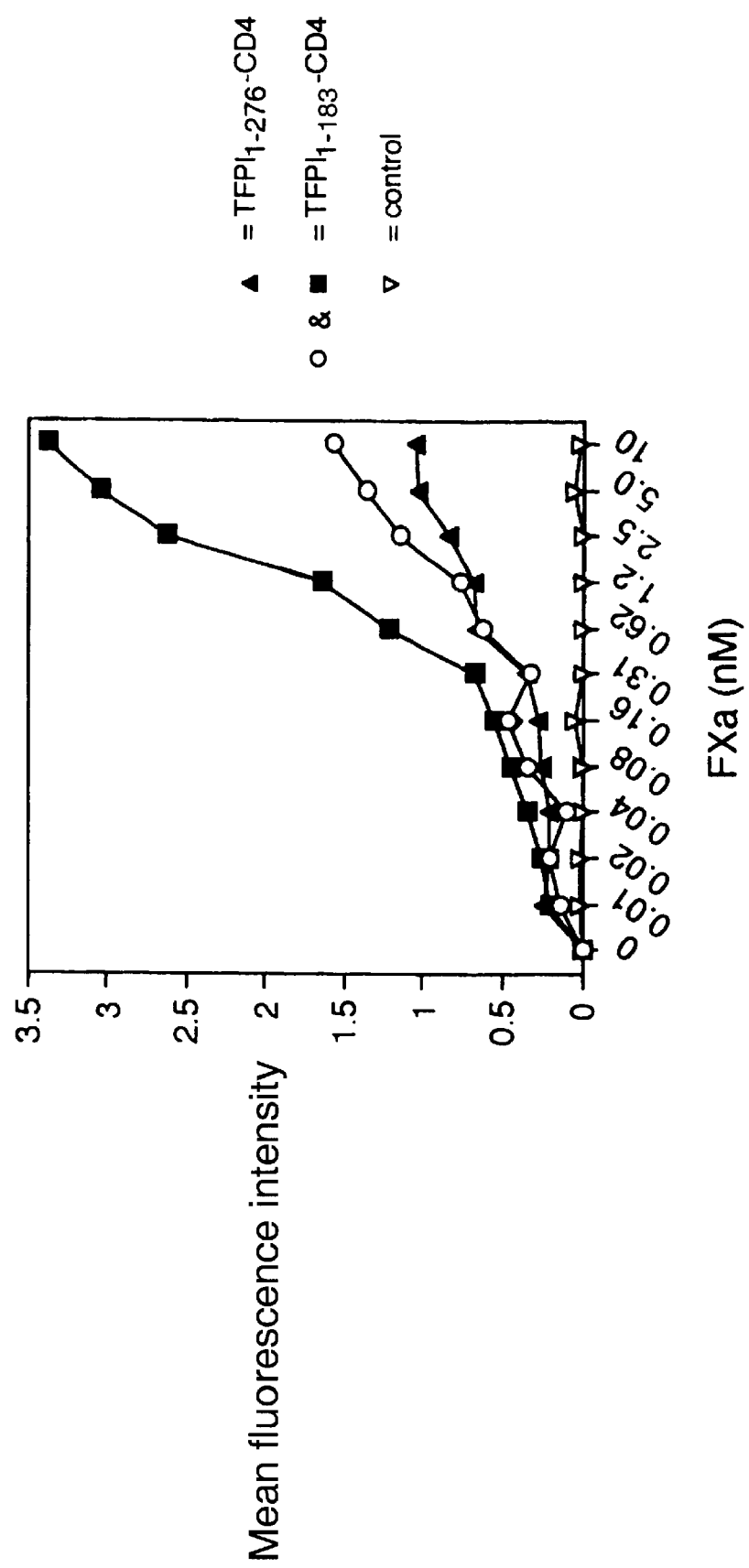
FIG. 10 shows specific FXa binding to cell surface bound $TFPI_{1-276}$-CD4 and $TFPI_{1-183}$-CD4.
Figure 12:
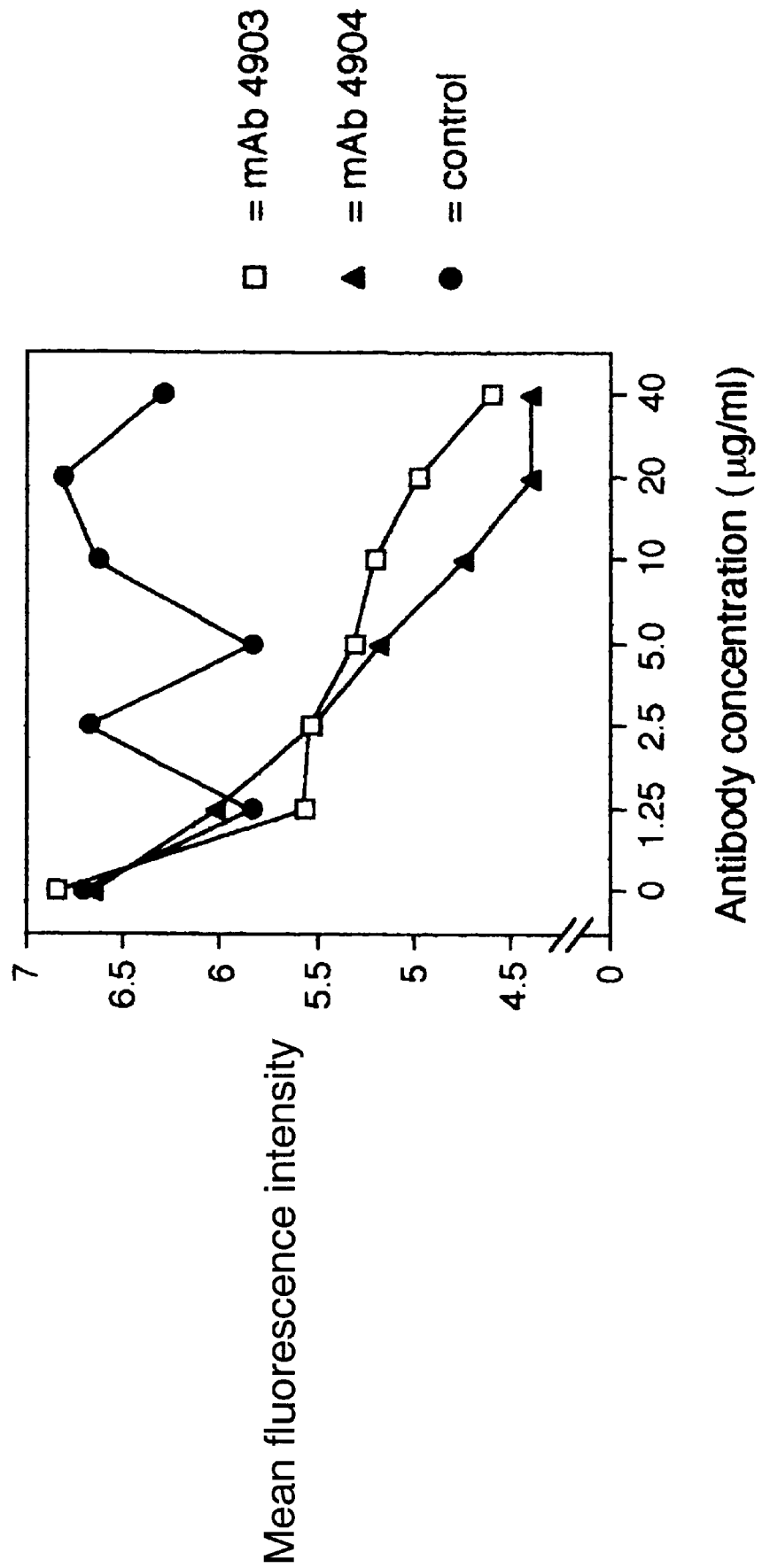
FIG. 12 shows the blocking of FXa binding by monoclonal antibodies directed against Kunitz domains I and II.
Figure 13:
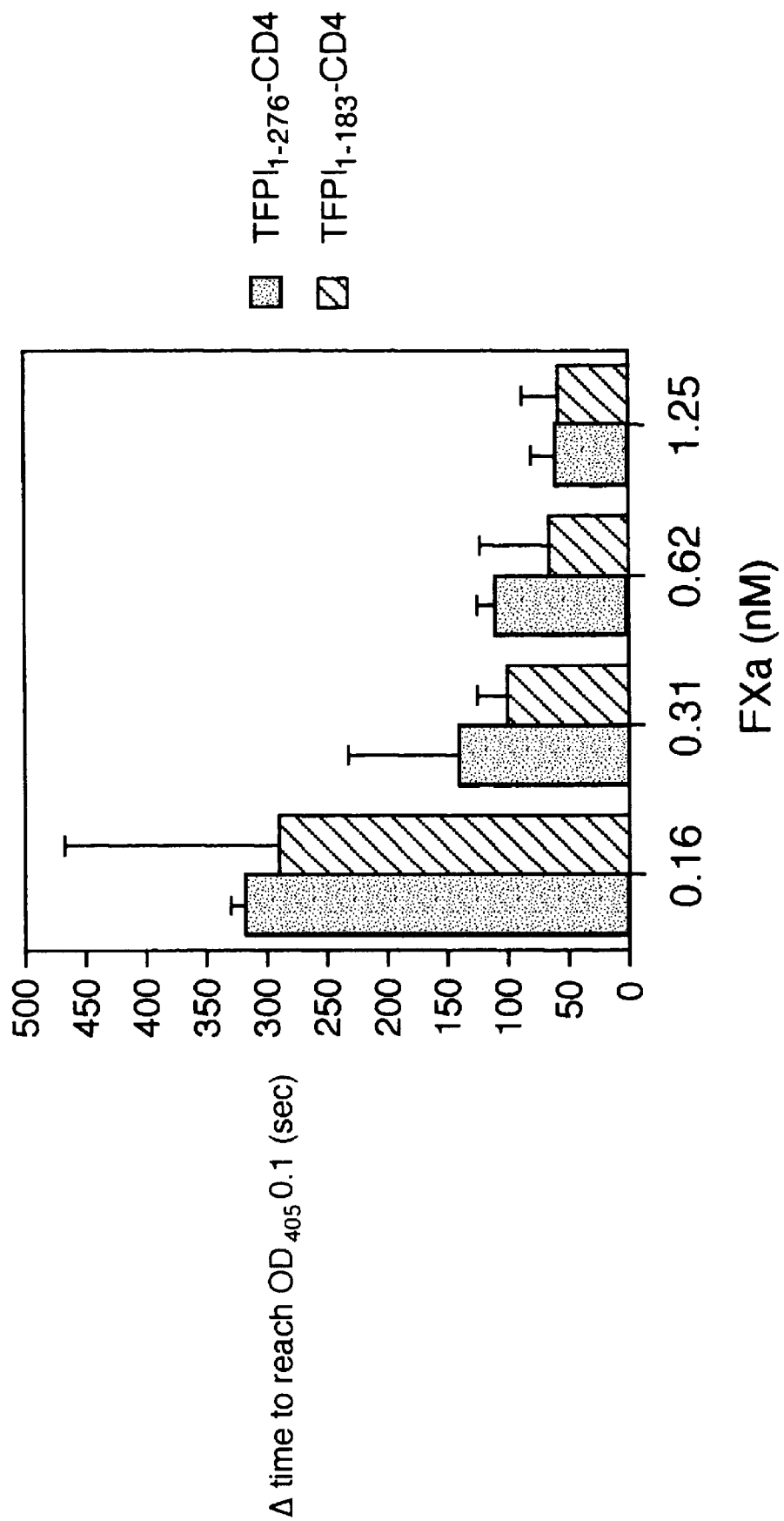
FIG. 13 shows the inhibition of FXa by cells expressing $TFPI_{1-276}$-CD4 and $TFPI_{1-183}$-CD4. The mean time for a FXa-specific chromogenic substrate to reach $OD_{405}$=0.1 is shown for transfected DAP.3 cells incubated with FXa. Values for control cells were subtracted and error bars indicate standard deviations.

7. Full Length and Truncated TFPI Anchored to CD4 Domains is Expressed at the Cell Surface In order to tether TFPI to the cell membrane, a fusion protein consisting of human $CD4_{166-435}$ linked either to full length TFPI including all three Kunitz domains ($TFPI_{1-276}$) or to a truncated form of TFPI lacking Kunitz domain III and the C-terminal ($TFPI_{1-183}$) (Wun, 1988) (FIG. 8). These were synthesized in a similar way to that described above for hirudin, with the TFPI and CD4 sequences being fused using a cassette cloning strategy, but unlike hirudin, TFPI is a mammalian protein and hence contains an endogenous signal peptide.

DNA encoding the N-terminal portion of TFPI including Kunitz domains I and II (675 bp) was amplified using the primers:

5'-catcgtcgacggatctagatgatacacaatgaagaaagtacatgacatgggc-3' <SEQ ID 12>

(introducing SalI and BamHI restriction sites); and

5'-ggacctgcagaattcaaaaaggctgg-3' <SEQ ID 13>

(containing EcoRI and PstI sites).

DNA encoding the third Kunitz domain together with the C-terminal end of TFPI (315 bp) was amplified using primers:

5'-agcctttttgaattccacggtccctcat-3' <SEQ ID 14>

(with an EcoRI site); and

5'-cattgctataacaactgcagatatttttaac-3' <SEQ ID 15>

(containing a PstI site).

$CD4_{166-435}$ was amplified as described above.

By the introduction of restriction sites into the 3' end of the $TFPI_{1-183}$ cDNA and the 5' end of the $TFPI_{184-276}$ cDNA, $H^{184}$ and $G^{185}$ were mutated to $C^{184}$ and $R^{185}$ in the recombinant fusion proteins (FIG. 8). Furthermore, $P^{186}$ was mutated to $S^{186}$. The stop codon of TFPI was removed by introducing a PstI site, thus mutating $M^{276}$ to $I^{276}$, and the addition of amino acid $C^{277}$. In the course of introducing a PstI site in the N-terminal end of CD4 domain 3, $L^{164}$ and $Q^{165}$ were mutated to $C^{164}$ and $R^{165}$, respectively. In the $TFPI_{184-276}$ cDNA, $K^{265}$ was found to be mutated to $E^{265}$ and in $CD4_{166-435}$ $V^{328}$ was mutated to $A^{328}$ (as described above).

All PCR products were cloned into pBluescript SK(+).

The complete TFPI-CD4 cDNAs were ligated into the BamHI site of the pHβActpr-1gpt expression vector.

As above, DAP.3 cells, maintained in supplemented DMEM were transfected with calcium-phosphate as above. Clones were analysed for TFPI and CD4 expression by FACS using murine anti-human TFPI mAbs 4903 or 4904 (American Diagnostica), both at 10 µg/ml, and an undiluted OKT-4 hybridoma supernatant (Reinherz, 1979). 4903 is directed against Kunitz domain 1, whereas 4904 is directed against Kunitz domain II. $10^5$ cells for each sample were analysed and, as above, cell line 531 was used as a control.

As shown in FIG. 9, both $TFPI_{1-276}$-CD4 and $TFPI_{1-183}$-CD4 can be expressed at the cell surface.

8. $TFPI_{1-183}$-CD4 and $TFPI_{1-276}$-CD4 Tethered to the Cell Surface Confer FXa Binding To test whether TFPI tethered in this way to the cell surface retains its FXa binding activity, the following binding assay was used.

Stably transfected DAP.3 cells were detached by treatment with PBS, 5 mM EDTA for 10 minutes at 37° C. After 4 washes with excess PBS, 0.1% BSA (w/v), $2.5\times10^5$ cells in 100 μl were incubated for 1 hour at 37° C. with increasing concentrations of FXa.

Cells were then washed twice and further incubated for 30 minutes on ice with 10 μg/ml rabbit anti-human FXa immunoglobulins (RAFX-IG, Enzyme Research Laboratories) in 100 μl. After two additional washes, cells were incubated for 30 minutes with FITC-conjugated swine anti-rabbit polyclonal imnmunoglobulins and analysed by flow cytometry.

As shown in FIG. 10, DAP.3 cells expressing $TFPI_{1-276}$-CD4 and $TFPI_{1-183}$-CD4 at the cell surface strongly bound FXa in a dose-dependent fashion (FIG. 10), with significant binding detected at 0.02 nM. No difference in FXa binding was detected between full length and truncated TFPI-CD4.

It was also possible to block FXa binding with a polyclonal anti-TFPI immunoglobulin fraction (4901) or with monoclonals 4903 and 4904.

Cells were incubated on ice for 30 minutes with 4901, 4903, or 4904 at increasing concentrations, using an anti-haemoglobin antiserum (Dakopatts) as a negative control. The cells were then washed twice in PBS, 0.1% BSA, and further incubated with 5 nM FXa for one hour at 37° C. The cells were then washed and incubated with RAFX-IG as above and analysed for FXa binding by FACS.

FXa binding to $TFPI_{1-276}$-CD4 decreased 27% and 55% at 10 and 80 μg/ml polyclonal 4901, respectively, compared with cells incubated with the irrelevant anti-haemoglobin polyclonal control (FIG. 11A). Diminished FXa binding was also found for $TFPI_{1-183}$-CD4 cells pre-incubated with 4901 (FIG. 11B).

When $TFPI_{1-276}$-$CD^4$ was blocked with either 4903 or 4904, 33% less FXa binding was observed at 40 μg/ml mAb, compared with isotype-matched mouse immunoglobulins (FIG. 12). No significant difference in blocking activity was detected between mAbs 4903 and 4904.

This demonstrates for the first time that TFPI retains its FXa binding activity when expressed as a membrane-bound fusion protein.

9. $TFPI_{1-183}$-CD4 and $TFPI_{1-276}$-CD4 are Both Functionally Active Against FXa To determine whether TFPI tethered to the cell surface retained its ability to inhibit the function of FXa, the proteolytic activity of FXa was analysed using the chromogenic substrate N-a-Z-D-Arg-Gly-Arg-pNA.2HCl ("S-2765") (Quadratech).

Transfected DAP.3 cells were detached as described above and washed 4 times with excess TBS, pH 7.4, 0.1% BSA. $0.5\times10^6$ cells (in 100 μl) per well were incubated for 1 hour at 37° C. with various concentrations of FXa. 50 μl of 4 mM S-2765 were added and cells were further incubated for 2 hours at 37° C. $OD_{405}$ was measured every 30 seconds and the time required to reach $OD_{405}$=0.1 was determined, showing remaining active FXa.

FXa activity was inhibited by expressed TFPI-CD4 in a dose dependent manner with the greatest inhibition noted when low concentrations of FXa (0.16 nM) were added (FIG. 13). In a series of experiments, no significant difference in FXa inhibition was observed between cells expressing $TFPI_{1-183}$-CD4 or $TFPI_{1-276}$-CD4.

Thus, Kunitz domain II retains its function when tethered to the cell surface in both $TFPI_{1-183}$-CD4 and $TFPI_{1-276}$-CD4.

10. $TF_{1-219}$/FVIIa Complex Binds Irrespectively of the Presence of the Third Kunitz Domain Binding of tissue factor and factor VIIa can be used to confirm whether Kunitz domain I also retains its function.

Recombinant human TF$_{1-219}$ and FVIIa were produced in E. coli and CHO-K1, respectively (O'Brien, 1994). These were mixed in equimolar concentrations and incubated at 25° C. for 15 minutes to obtain a TF$_{1-219}$/FVIIa complex.

Polyclonal rabbit immunoglobulins against human TF were produced according to standard methods.

DAP.3 cells expressing either TFPI$_{1-276}$-CD4 or TFPI$_{1-183}$-CD4 were incubated with 5 nM FXa for 1 hour at 37° C. Cells were washed twice and TFI$_{1-219}$/FVIIa complex was added to 2.5×10$^5$ cells in 100 μl. After 1 hour at 37° C. transfectants were washed twice and incubated with 50 μl polyclonal rabbit anti-TF immunoglobulins (2.5 μg/ml) for 30 minutes on ice followed by 2 washes, and further incubation with FITC-conjugated swine anti-rabbit immunoglobulins. Positive cells were analysed by flow cytometry.

Figure 14B:
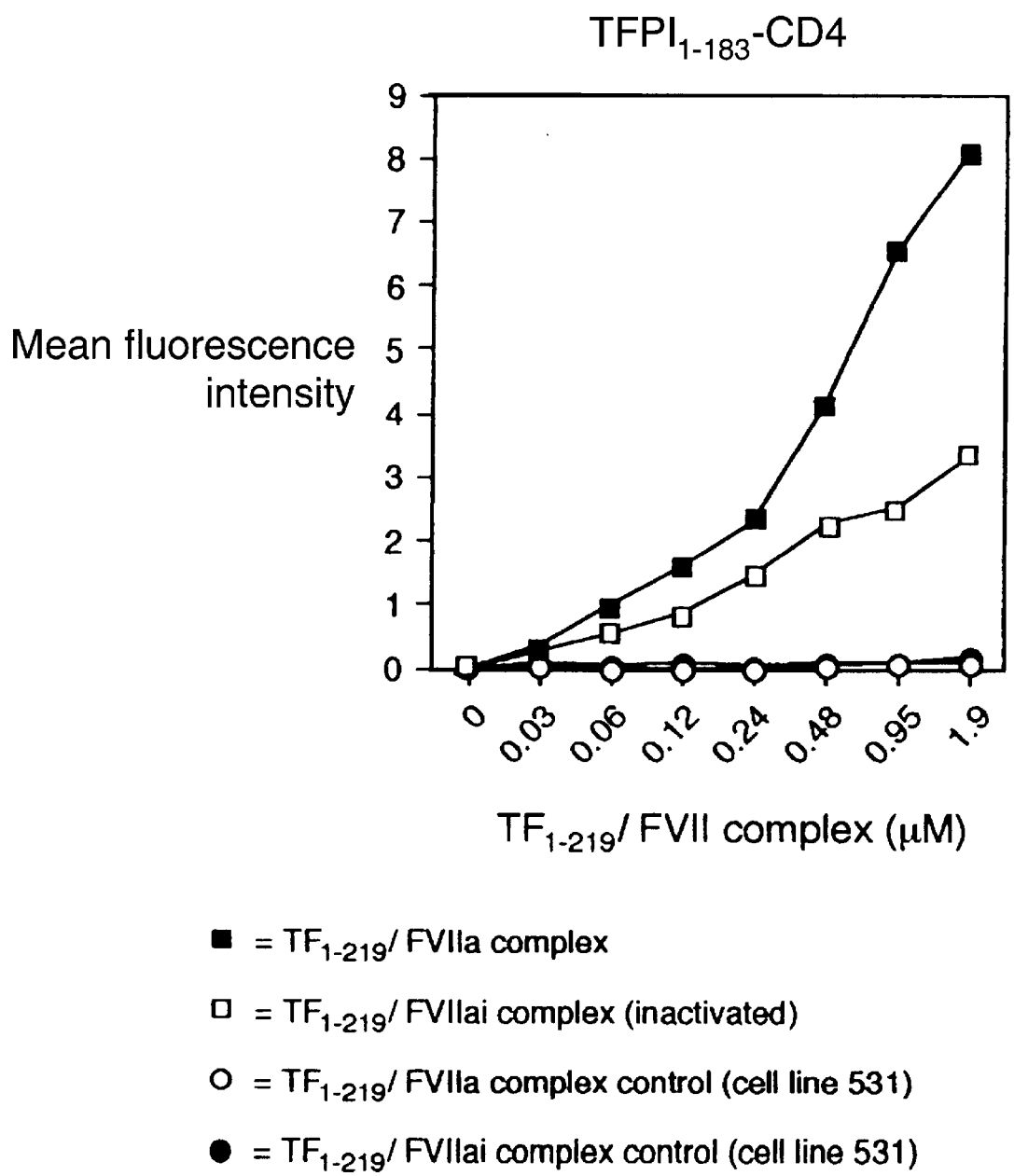
FIG. 14 shows that an active $TF_{1-219}$/FVIIa complex is required for maximal binding to TFPI-CD4 chimeric proteins.

TF$_{1-219}$/FVIIa bound equally efficient to both TFPI$_{1-276}$-CD4 (FIG. 14A) and TFPI$_{1-183}$-CD4 (FIG. 14B), while no binding at all was detected to control cell line 531.

To confirm specific binding to Kunitz domain I by the TF$_{1-219}$/FVIIa complex, FVIIa was inactivated by pre-incubation with 1,5-dansyl-Glu-Gly-Arg-chloromethyl ketone, dihydrochloride ("1,5-DNS-GGACK.HCl"). This binds to the active site of FVIIa and inhibits binding to TFPI whilst not affecting the formation of the TF$_{1-219}$/FVIIa complex (Bajaj, 1992).

FVIIa was first incubated with a 100-fold molar excess of 1,5-DNS-GGACK•HCl for 18 hours at 20° C. and repurified by ion-exchange chromatography. Active-site inhibited FVIIa (FVIIai) was incubated with an equimolar concentration of TF$_{1-219}$ at 25° C. for 15 minutes and then added to 2.5×10$^5$ cells in 100 μl. Subsequent steps were as described above.

As can be seen from FIG. 14, significantly less TF$_{1-219}$/FVIIai complex bound to TFPI-CD4 expressing cells as compared to bound "active" TF$_{1-219}$/FVIIa. No difference was observed between DAP.3 transfected with TFPI$_{1-276}$-CD4 or TFPI$_{1-183}$-CD4.

Thus Kunitz domain I also retains its function when tethered to the cell surface in TFPI$_{1-183}$-CD4 and TFPI$_{1-276}$-CD4. It is therefore apparent that TFPI tethered at the cell surface is functionally active as a whole.

Figure 18A:
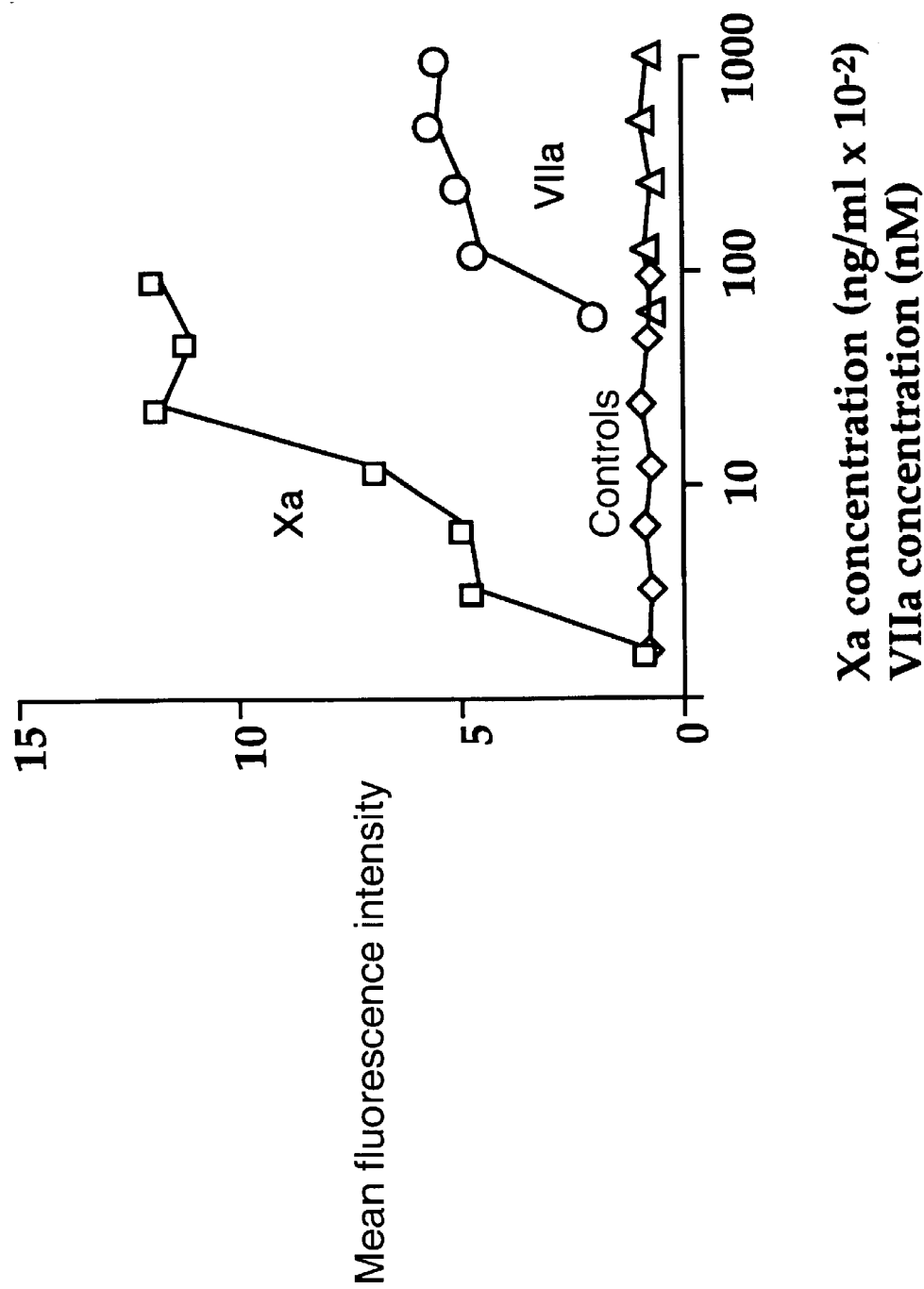
Figure 19B:
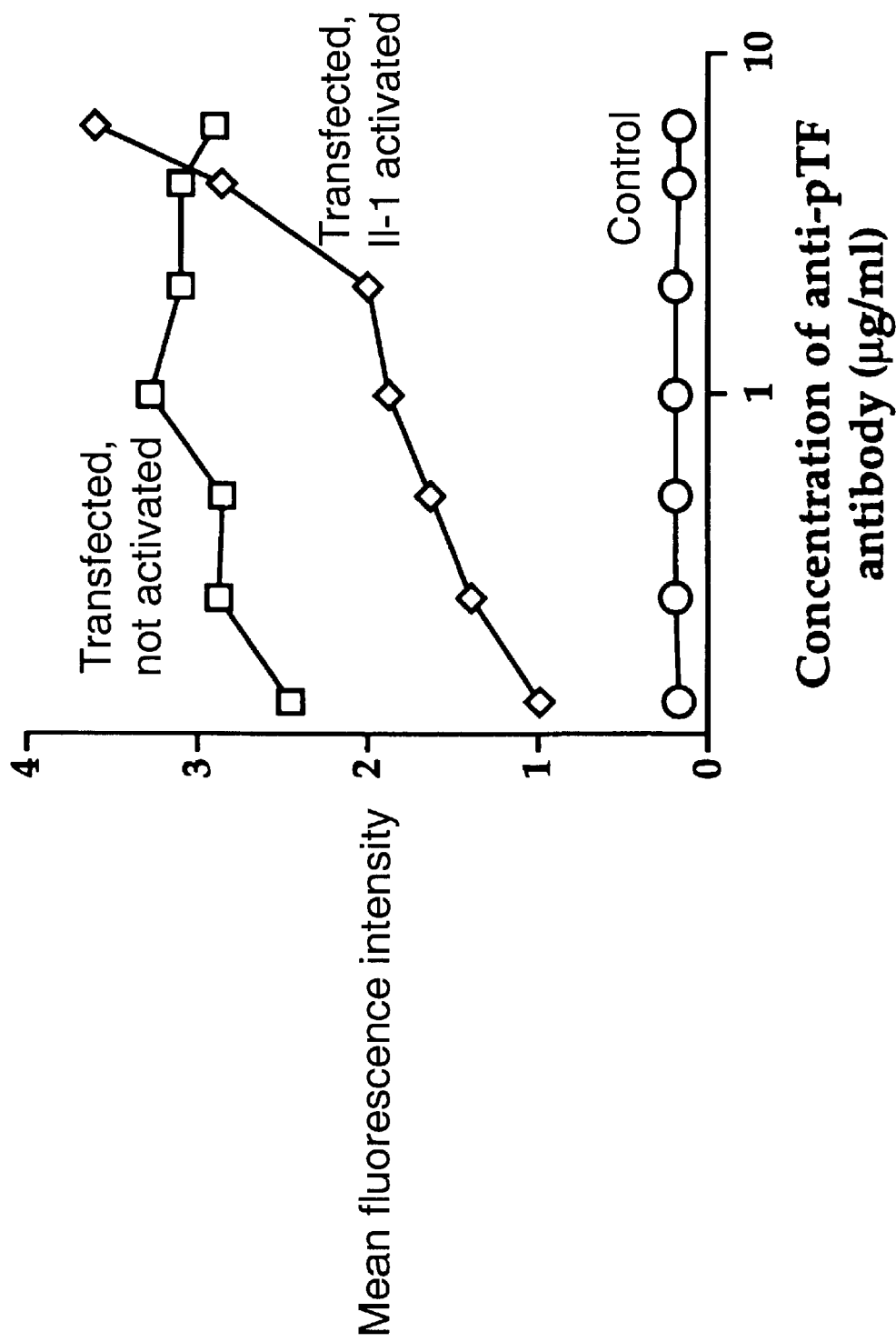

11. TFPI-CD4 Expressed on IPEC Binds Relevant Human Clotting Factors and Porcine TF As shown in FIG. 18, the TFPI-CD4 fusion protein can be expressed on IPEC and retains the ability to bind FXa and FVIIa. To demonstrate that TFPI can physically interact with porcine TF, a competitive inhibition approach using soluble human TF was adopted. As shown in FIG. 19A, in the presence of saturating concentrations of FXa and FVIIa, the binding of soluble human TF to TFPI-transfected IPEC (pre-treated with IL-1α) was significantly reduced compared to the binding by TF-negative control transfectants (not IL-1α activated). This suggests that porcine TF was competing with soluble human TF for VIIa, and therefore for TFPI binding. FIG. 19B supports this, showing that binding of soluble human TF to TFPI-CD4-transfected IPEC (IL-1α pre-activated) was increased if the transfectants were incubated with increasing concentrations of antibody against porcine TF. The effect of this antibody could reflect inhibition of the interaction between porcine TF and FVIIa, or between porcine TF-VIIa complexes and TFPI-CD4. Either way, the results suggest that the TFPI-CD4-fusion protein expressed on the surface of IPEC physically interacts with porcine TF-FVIIa.

12. TFPI-CD4 Expressed on IPEC Inhibits TF-dependent Fibrin Generation

Figure 20B:
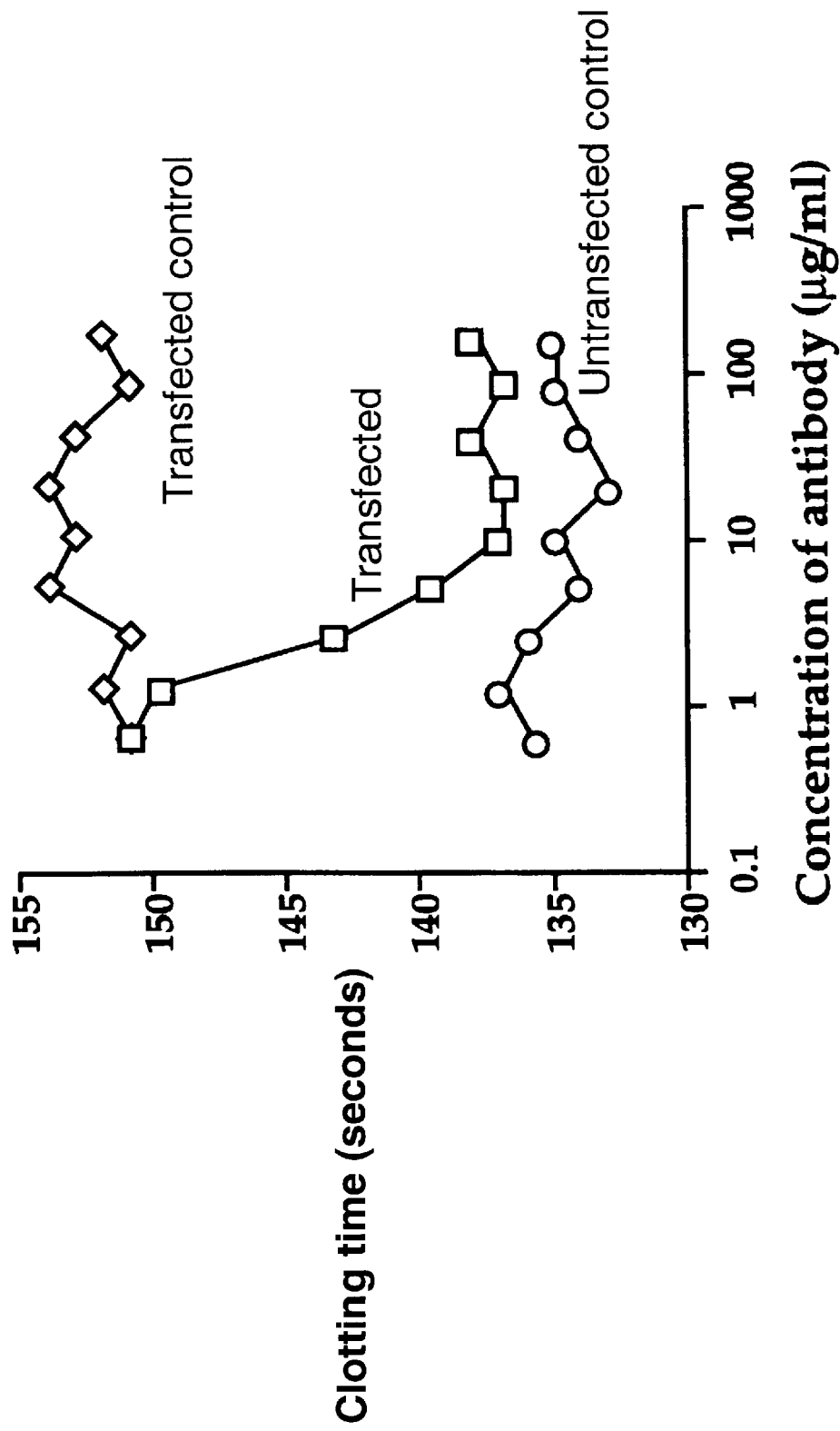

FIG. 20A shows the results of a single representative experiment to illustrate the procoagulant phenotype of TFPI-CD4-transfected IPEC. The presence of the fusion protein on transfected cells consistently prolonged clotting times when compared with control IPEC. This effect was only observed, however, after IL-1α activation—TFPI-CD4 expression had no influence on clotting times when TF-negative IPEC were used. Thus, the TFPI-CD4, as expected, inhibited TF-dependent, but not TF-independent fibrin generation. An anti-TFPI antibody, used in increasing concentrations during a pre-incubation step, was able to normalise clotting times back to those seen with untransfected IL-1α-activated control IPEC (FIG. 20B), indicating that the prolongation of clotting times in the presence of the transfected cells was due entirely to the specific inhibitory action of TFPI.

13. Expression of a Protein C Activator at the Cell Membrane

To express heterologous constructs comprising the protein C activator isolated from the venom of Agkistrodon contortrix contortrix (McMullen, 1989; Kisiel, 1987), a cDNA encoding the protein was synthesised. The protein sequence is <SEQ ID 16>:

V I G G D E C N I N E H R F L A L V Y A N G S L C
G G T L I N Q E W V L T A R H C D R G N M R I
Y L G M H N L K V L N K D A L R R F P K E K Y
F C L N T R N D T I W D K D I M L I R L N R P V
R N S A H I A P L S L P S N P P S V G S V C R I M
G W G T I T S P N A T L P D V P H C A N I N I L
D Y A V C Q A A Y K G L A A T T L C A G I L E G
G K D T C K G D S G G P L I C N G Q F Q G I L
S V G G N P C A Q P R K P G I Y T K V F D Y T D
W I Q S I I S G N T D A T C P P

In accordance with porcine codon-usage bias (which is applicable to most, if not all, mammalian cells), the following single stranded DNA was synthesised <SEQ ID 17>:

```
GTG ATC GGC GGC GAC GAG TGC AAC ATC AAC GAG CAC CGC
TTC CTG GCC CTG GTG TAC GCC AAC GGC AGC CTG TGC GGC
GGC ACC CTG ATC AAC CAG GAG TGG GTG CTG ACC GCC CGC
CAC TGC GAC CGC GGC AAC ATG CGC ATC TAC CTG GGC ATG
CAC AAC CTG AAG GTG CTG AAC AAG GAC GCC CTG CGC CGC
TTC CCC AAG GAG AAG TAC TTC TGC CTG AAC ACC CGC AAC
GAC ACC ATC TGG GAC AAG GAC ATC ATG CTG ATC CGC CTG
AAC CGC CCC GTG CGC AAC AGC GCC CAC ATC GCC CCC CTG
AGC CTG CCC AGC AAC CCC CCC AGC GTG GGC AGC GTG TGC
CGC ATC ATG GGC TGG GGC ACC ATC ACC AGC CCC AAC GCC
ACC CTG CCC GAC GTG CCC CAC TGC GCC AAC ATC AAC ATC
CTG GAC TAC GCC GTG TGC CAG GCC GCC TAC AAG GGC CTG
GCC GCC ACC ACC CTG TGC GCC GGC ATC CTG GAG GGC GGC
AAG GAC ACC TGC AAG GGC GAC AGC GGC GGC CCC CTG ATC
TGC AAC GGC CAG TTC CAG GGC ATC CTG AGC GTG GGC GGC
AAC CCC TGC GCC CAG CCC CGC AAG CCC GGC ATC TAC ACC
AAG GTG TTC GAC TAC ACC GAC TGG ATC CAG AGC ATC ATC
AGC GGC AAC ACC GAC GCC ACC TGC CCC CCC
```

This single-stranded DNA was annealed to complementary oligonucleotides to give a double-stranded molecule.

Restriction sites are included at either end of the double-stranded DNA, to which is ligated a CD4 anchor and a P-selectin signal sequence in a similar way to that described above. The resulting molecule was ligated, as before, into the pH Actpr-1 gpt vector.

As an alternative DNA source, a snake cDNA library could be screened on the basis of the known protein sequence.

Figure 21A:
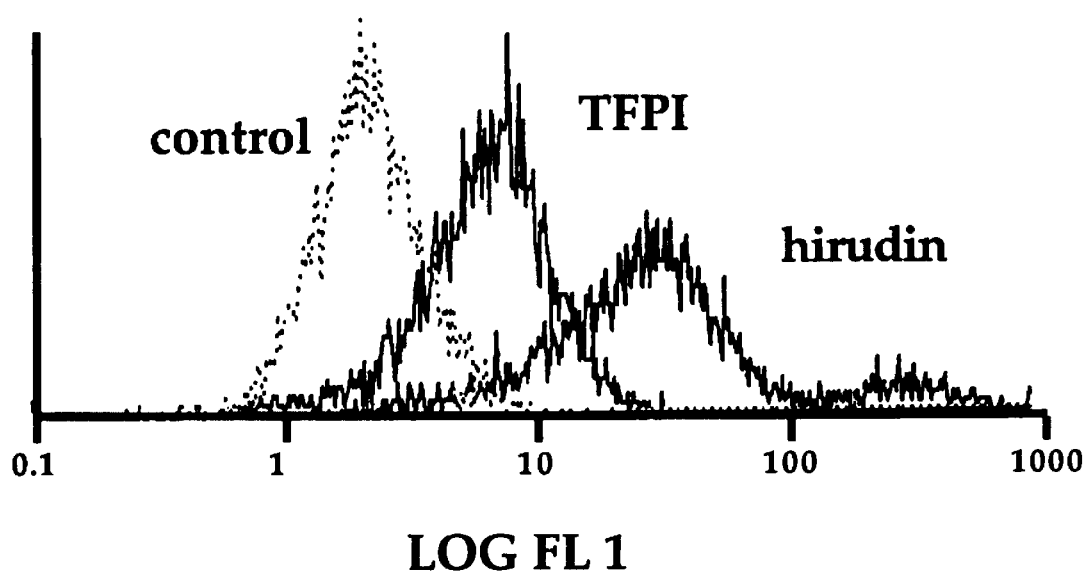

14. Co-expression of TFPI-CD4 and Hirudin-CD5 Causes Inhibition of TF-dependent and TF-independent Clotting Stable transfectants expressing both TFPI-CD4 and hirudin-CD4 were generated. As shown in FIG. 21A, the primary transfectants expressed variable levels of hirudin and low levels of TFPI. Despite this modest expression by the majority of transfectants, however, the procoagulant phenotype of these cells was significantly reduced compared to controls (FIG. 21B). The cell-surface presence of both anticoagulant molecules on IL-1$\alpha$-activated IPEC markedly prolonged the time to clot plasma to approximately 300 seconds, which is approaching the time taken for recalcified human plasma to clot spontaneously. Blocking studies with anti-hirudin and anti-TFPI antibodies confirmed that the altered phenotype of these double transfectants was due to specific inhibition of coagulation by the expressed hirudin and TFPI.

It will be understood that the invention is described above by way of example only and modifications may be made whilst remaining within the scope and spirit of the invention.

REFERENCES (THE CONTENTS OF WHICH ARE INCORPORATED HEREIN)

Bach F H, Winkler H, Ferran C, Hancock W W, Robson S C. Delayed xenograft rejection. *Immunology Today* 1996; 17(8); 379–384.

Bajaj S P, Sabharwal A K, Gorka J, Birktoft J J. Antibody-probed conformational transitions in the protease domain of human factor IX upon calcium binding and zymogen activation: putative high-affinity $Ca^{2+}$-binding site in the protease domain. *PNAS USA* 1992; 89:152–156.

Bradley A, Liu P. Target practice in transgenics. *Nature Genet*. 1996; 14:121–123.

Clarke A R. The adenovirus and the egg: a new approach to transgenesis. *Nature Biotech*. 1996; 14:942.

Dang Q D, Guinto E R, Di Cera E. Rational engineering of activity and specificity in a serine protease. *Nature Biotech*. 1997; 15:146–149.

Diamond L E, McCurry K R, Oldharn E R, Tone M, Waldmann H, Platt J L, Logan J S. Human CD59 expressed in transgenic mouse hearts inhibits the activation of complement. *Transplant Immunol*. 1995; 3:305–312.

Disdier M, Morrissey J H, Fugate R D, Bainton D F, McEver R P. Cytoplasmic domain of P-selectin (CD62) contains the signal for sorting into the regulated secretory pathway. *Molec. Biol. Cell*. 1992; 3:309–321.

Dodt J, Kohler S, Baici A. Interaction of site specific hirudin variants with alpha-thrombin. *FEBS Lett*. 1988; 229:87–90

Green S A, Setiadi H, McEver R P, Kelly R B. The cytoplasmic domain of P-selectin contains a sorting determinant that mediates rpaid degradation in lysosomes. *J. Cell. Biol*. 1994; 124:435–448.

Gunning P, Leavitt J, Muscat G, Ng S Y, Kedes L. A human beta-actin expression vector system directs high-level accumulation of antisense transcripts. *PNAS USA*. 1987; 84:4831–5

Hamamoto T, Yamamoto M, Nordfang O, Petersen J G L, Foster D C, Kisiel W. Inhibitory properties of full-length and truncated recombinant TFPI variants expressed in *Saccharomyces cereviaiae*. *J. Biol. Chem*. 1993; 268:13344–13351.

Heckl-Östreicher B, Binder R, Kirschfink M. Functional activity of the membrane-associated complement inhibitor CD59 in a pig-to-human in vtiro model for hyperacture xenograft rejection. *Clin. Exp. Immunol*. 1995; 102:589–595.

Holmes N, Ennis P, Wan A M, Denney D W, Parham P. Multiple genetic mechanisms have contributed to the generation of the HLA-A2/A28 family of class 1 MHC molecules. *J. Immunol*. 1987; 139:936–441

Johnston G I, Cook R G, McEver R P. Cloning of GMP-140, a granule membrane protein of platelets and endothelium: sequence similarity to proteins involved in cell adhesion and inflammation. *Cell*. 1989; 56:1033–44

Kiely J-M, Cybulsky M I, Luscinskas F W, Gimbome M A. Immunoselective targeting of an anti-thrombin agent to the surface of cytokine-activated vascular endothelial cells. *Arterioscler. Thromb. Vasc. Biol*. 1995; 15:1211–1218.

Kisiel E, Kondo S, Smith K J, McMullen B A, Smith L F. Characterization of a protein C activator from *Agkistrodon contortrix contortrix* venom. *J. Biol. Chem*. 1987; 262:12607–13.

Knapp A, Degenhardt T, Dodt J. Hirudisins. *J. Biol. Chem*. 1992; 34:24230–24234.

Langford G A, Cozzi E, Yannoutsos N, Lancaster R, Elsome K, Chen P, White D G J. Production of pigs transgenic for human regulators of complement activation using YAC technology. *Transplant Proc*. 1996; 28:862–863.

Lechler R I, Bal V, Rothbard J B, Germain R N, Sekaly R, Long E O, Lamb J. Structural and functional studies of HLA-DR restricted antigen recognition by human helper T lymphocyte clones by using transfected murine cell lines. *J. Immunol*. 1988; 141:3003–3009.

McCurry K R, Diamond L E, Kooyman D L, Byrne G W, Martin M J, Logan J S, Platt J L. Human complement regulatory proteins expressed in transgenic swine protect swine xenografts from humoral injury. *Transplant Proc*. 1996; 28:758.

McMullen B A, Fujikawa K, Kisiel W. Primary structure of a protein C activator from *Agkistrodon contortrix contortrix* venom. *Biochemistry* 1989; 28:674–679.

Maddon P J, Littman D R, Godfrey M, Maddon D E, Chess L, Axel R. The isolation and nucleotide sequence of a cDNA encoding the T cell surface protein T4: a new member of the immunoglobulin gene family. *Cell* 1985; 42:93–104

Mao S S, Huang J, Welebob C, Neeper M P, Garsky V M, Shafer J A. Identification and characterization of variants of tick anticoagulant peptide with increased inhibitory potency toward human factor Xa. *Biochemistry* 1995; 34:5098–5103.

Merkenschlager M, Altmann D M, Ikeda H. T cell allore-sponses against HLA-DQ and -DR products involve multiple epitopes on the CD4 molecule. Distinct mechanisms contribute to the inhibition of HLA class Independent and -independent T cell responses by antibodies to CD4. *J. Immunol*. 1990; 145:3181–7.

O'Brien D P, Kemball-Cook G, Hutchinson A M, Martin D M, Johnson D J, Byfield P G. Takamiya O, Tuddenham E G, McVey J H. Surface plasmon resonance studies of the interaction between factor VII and tissue factor. *Biochemistry* 1994; 33:14162–9.

Reinherz E L, Kung P C, Goldstein G, Schlossman S F. Separation of functional subsets of human T cells by a monoclonal antibody. *PNAS USA*. 1979; 76:4061–4065

Schlaeppi J M. Preparation of monoclonal antibodies to the thrombin/hirudin complex. *Thromb Res*. 1991; 62:459–470

Skem T, Bischoff R, Jallat S, Dott K, Ali-Hadji D, Clesse D, Kieny M P, Courtney M. Sulphation of hirudin in BHK cells. *FEBS*. 1990; 1:36–38.

Squinto S P. Xenogeneic organ transplantation. *Curr. Opin. Biotech*. 1996; 7:641–645.

Wagner D D. The Weibel-Palade body: the storage granule for von Willebrand factor and P-selectin. *Thrombosis & Haemostasis*. 1993; 70:105–110.

Wheeler M B. Development and validation of swine embryonic stem cells: a review. *Reprod Fertil. Dec.* 1994; 6:563–568.

White D, Cozzi E, Langford G, Oglesby T, Wang M, Wright L, Wallwork J. The control of hyperacute rejection by genetic engineering of the donor species. *Eye* 1995; 9:185–189.

Wun T C, Kretzmer K K, Girard T J, Miletich J P, Broze G J. Cloning and characterization of a cDNA coding for the lipoprotein-associated coagulation inhibitor shows that it consists of three tandem Kunitz-type inhibitory domains. *J. Biol. Chem.* 1988; 263:6001–4

Yannoutsos N, Langford G A, Cozzi E, Lancaster R, Elsome K, Chen P, White D J G. Production of pigs transgenic for human regulators of complement activation. *Transplant Proc*. 1995; 27:324–325.

What is claimed is:

1. A protein comprising (i) a region with anticoagulant activity, (ii) a transmembrane sequence from a membrane protein that can anchor said protein to a cell membrane; and (iii) a target sequence which can target a nascent polypeptide to a secretory granule, thereby preventing the protein from being constitutively expressed at the cell surface.

2. A protein according to claim 1, wherein the anticoagulant region comprises the sequence of a hirudin, a tissue factor pathway inhibitor, a tick anticoagulant peptide, or a protein C activator.

3. A protein according to claim 1 wherein said secretory granule does not fuse with the cell's plasma membrane until the cell is suitably stimulated.

4. A protein according to claim 3, wherein said secretory granule is a Weibel-Palade body.

5. A protein according to claim 4 wherein said targeting sequence is the cytoplasmic domain of P-selectin.

6. A protein according to claim 1 wherein said anchor sequence is that of P-selectin.

7. A polynucleotide encoding a protein according to claim 1.

8. A vector comprising a polynucleotide according to claim 7.

9. A delivery system comprising a protein of claim 1, a polynucleotide encoding said protein or a vector comprising said polynucleotide.

* * * * *

UNITED STATES PATENT AND TRADEMARK OFFICE
CERTIFICATE OF CORRECTION

PATENT NO.     : 6,423,316 B1                                   Page 1 of 1
DATED          : July 23, 2002
INVENTOR(S)    : Kristian Riesbeck et al.

It is certified that error appears in the above-identified patent and that said Letters Patent is hereby corrected as shown below:

<u>Title page,</u>
Item [73], Assignee, delete "Imperial College Innovative Limited" and substitute
-- Imperial College Innovations Limited --.

Signed and Sealed this

First Day of April, 2003

JAMES E. ROGAN
*Director of the United States Patent and Trademark Office*

SEQUENCE LISTING

```
<160> NUMBER OF SEQ ID NOS: 17

<210> SEQ ID NO 1
<211> LENGTH: 37
<212> TYPE: DNA
<213> ORGANISM: Artificial Sequence
<220> FEATURE:
<223> OTHER INFORMATION: PCR primer

<400> SEQUENCE: 1
cagtgtcgac ggatccatgg ccgtcatggc gccccga                              37

<210> SEQ ID NO 2
<211> LENGTH: 34
<212> TYPE: DNA
<213> ORGANISM: Artificial Sequence
<220> FEATURE:
<223> OTHER INFORMATION: PCR primer

<400> SEQUENCE: 2
gtcagtgtaa acaaccgccc aggtctgggt cagg                                 34

<210> SEQ ID NO 3
<211> LENGTH: 36
<212> TYPE: DNA
<213> ORGANISM: Artificial Sequence
<220> FEATURE:
<223> OTHER INFORMATION: PCR primer

<400> SEQUENCE: 3
acccagacct gggcggttgt ttacactgac tgcacc                               36

<210> SEQ ID NO 4
<211> LENGTH: 37
<212> TYPE: DNA
<213> ORGANISM: Artificial Sequence
<220> FEATURE:
<223> OTHER INFORMATION: PCR primer

<400> SEQUENCE: 4
gacgctgcag aattcttgca ggtattcttc cgggatt                              37

<210> SEQ ID NO 5
<211> LENGTH: 24
<212> TYPE: DNA
<213> ORGANISM: Artificial Sequence
```

-continued

```
<220> FEATURE:
<223> OTHER INFORMATION: glycine linker oligonucleotide

<400> SEQUENCE: 5
aattaggagg ttctggaggc tgca                                        24

<210> SEQ ID NO 6
<211> LENGTH: 16
<212> TYPE: DNA
<213> ORGANISM: Artificial Sequence
<220> FEATURE:
<223> OTHER INFORMATION: glycine linker oligonucleotide

<400> SEQUENCE: 6
gcctccagaa cctcct                                                 16

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
tgtctgcagg aaccagaaga aggtggaatt ca                               32

<210> SEQ ID NO 8
<211> LENGTH: 28
<212> TYPE: DNA
<213> ORGANISM: Artificial Sequence
<220> FEATURE:
<223> OTHER INFORMATION: PCR primer

<400> SEQUENCE: 8
gtgggatccg cctggcctcg tgcctcaa                                    28

<210> SEQ ID NO 9
<211> LENGTH: 53
<212> TYPE: DNA
<213> ORGANISM: Artificial Sequence
<220> FEATURE:
<223> OTHER INFORMATION: PCR primer

<400> SEQUENCE: 9
gtctgaaacg ctttctgaag aagatgccta gcccaatgaa aagcaggagg ccg        53

<210> SEQ ID NO 10
<211> LENGTH: 42
<212> TYPE: DNA
<213> ORGANISM: Artificial Sequence
<220> FEATURE:
<223> OTHER INFORMATION: PCR primer

<400> SEQUENCE: 10
tgggctaggc atcttcttca gaaagcgttt cagacaaaaa ga                    42

<210> SEQ ID NO 11
<211> LENGTH: 25
<212> TYPE: DNA
<213> ORGANISM: Artificial Sequence
<220> FEATURE:
<223> OTHER INFORMATION: PCR primer

<400> SEQUENCE: 11
gaccaggatc cggacaggtc tctta                                       25
```

-continued

<210> SEQ ID NO 12
<211> LENGTH: 57
<212> TYPE: DNA
<213> ORGANISM: Artificial Sequence
<220> FEATURE:
<223> OTHER INFORMATION: PCR primer

<400> SEQUENCE: 12
catcgtcgac ggatcctaga tgatttacac aatgaagaaa gtacatgcac tttgggc 57

<210> SEQ ID NO 13
<211> LENGTH: 26
<212> TYPE: DNA
<213> ORGANISM: Artificial Sequence
<220> FEATURE:
<223> OTHER INFORMATION: PCR primer

<400> SEQUENCE: 13
ggacctgcag aattcaaaaa ggctgg 26

<210> SEQ ID NO 14
<211> LENGTH: 28
<212> TYPE: DNA
<213> ORGANISM: Artificial Sequence
<220> FEATURE:
<223> OTHER INFORMATION: PCR primer

<400> SEQUENCE: 14 agccttttg aattccacgg tccctcat 28

<210> SEQ ID NO 15
<211> LENGTH: 31
<212> TYPE: DNA
<213> ORGANISM: Artificial Sequence
<220> FEATURE:
<223> OTHER INFORMATION: PCR primer

<400> SEQUENCE: 15
cattgctata acaactgcag atatttttaa c 31

<210> SEQ ID NO 16
<211> LENGTH: 231
<212> TYPE: PRT
<213> ORGANISM: Agkistrodon contortrix contortrix

<400> SEQUENCE: 16
```
Val Ile Gly Gly Asp Glu Cys Asn Ile Asn Glu His Arg Phe Leu Ala
1               5                   10                  15

Leu Val Tyr Ala Asn Gly Ser Leu Cys Gly Gly Thr Leu Ile Asn Gln
            20                  25                  30

Glu Trp Val Leu Thr Ala Arg His Cys Asp Arg Gly Asn Met Arg Ile
        35                  40                  45

Tyr Leu Gly Met His Asn Leu Lys Val Leu Asn Lys Asp Ala Leu Arg
    50                  55                  60

Arg Phe Pro Lys Glu Lys Tyr Phe Cys Leu Asn Thr Arg Asn Asp Thr
65                  70                  75                  80

Ile Trp Asp Lys Asp Ile Met Leu Ile Arg Leu Asn Arg Pro Val Arg
                85                  90                  95

Asn Ser Ala His Ile Ala Pro Leu Ser Leu Pro Ser Asn Pro Pro Ser
            100                 105                 110

Val Gly Ser Val Cys Arg Ile Met Gly Trp Gly Thr Ile Thr Ser Pro
        115                 120                 125
```

```
Asn Ala Thr Leu Pro Asp Val Pro His Cys Ala Asn Ile Asn Ile Leu
    130                 135                 140

Asp Tyr Ala Val Cys Gln Ala Ala Tyr Lys Gly Leu Ala Ala Thr Thr
145                 150                 155                 160

Leu Cys Ala Gly Ile Leu Glu Gly Gly Lys Asp Thr Cys Lys Gly Asp
                165                 170                 175

Ser Gly Gly Pro Leu Ile Cys Asn Gly Gln Phe Gln Gly Ile Leu Ser
            180                 185                 190

Val Gly Gly Asn Pro Cys Ala Gln Pro Arg Lys Pro Gly Ile Tyr Thr
        195                 200                 205

Lys Val Phe Asp Tyr Thr Asp Trp Ile Gln Ser Ile Ile Ser Gly Asn
    210                 215                 220

Thr Asp Ala Thr Cys Pro Pro
225                 230

<210> SEQ ID NO 17
<211> LENGTH: 693
<212> TYPE: DNA
<213> ORGANISM: Agkistrodon contortrix contortrix

<400> SEQUENCE: 17
gtgatcggcg gcgacgagtg caacatcaac gagcaccgct tcctggccct ggtgtacgcc      60
aacggcagcc tgtgcggcgg caccctgatc aaccaggagt gggtgctgac cgcccgccac     120
tgcgaccgcg gcaacatgcg catctacctg ggcatgcaca acctgaaggt gctgaacaag     180
gacgccctgc gccgcttccc caaggagaag tacttctgcc tgaacacccg caacgacacc     240
atctgggaca aggacatcat gctgatccgc ctgaaccgcc ccgtgcgcaa cagcgcccac     300 atcgccccc tgagcctgcc cagcaacccc cccagcgtgg gcagcgtgtg ccgcatcatg      360
ggctggggca ccatcaccag ccccaacgcc accctgcccg acgtgcccca ctgcgccaac     420
atcaacatcc tggactacgc cgtgtgccag gccgcctaca agggcctggc cgccaccacc     480
ctgtgcgccg gcatcctgga gggcggcaag gacacctgca agggcgacag cggcggcccc     540
ctgatctgca acggccagtt ccagggcatc ctgagcgtgg gcggcaaccc ctgcgcccag     600
ccccgcaagc ccggcatcta caccaaggtg ttcgactaca ccgactggat ccagagcatc     660
atcagcggca acaccgacgc cacctgcccc ccc                                  693
```